United States Patent

Miyake

[19]

[11] Patent Number: 5,835,190
[45] Date of Patent: Nov. 10, 1998

[54] OPHTHALMOLOGIC CURVATURE MEASURING DEVICE AND METHOD TO CONJOINTLY MEASURE A CENTRAL AND PERIPHERAL PORTION OF A CURVED SURFACE

[75] Inventor: Nobuyuki Miyake, Hiratuka, Japan

[73] Assignee: Nikon Corporation, Tokyo, Japan

[21] Appl. No.: 838,779

[22] Filed: Apr. 10, 1997

[30] Foreign Application Priority Data

Apr. 12, 1996 [JP] Japan .................................. 8-091512

[51] Int. Cl.$^6$ .................. A61B 3/10; A61B 3/00
[52] U.S. Cl. .................. 351/212; 351/221; 351/247
[58] Field of Search .................. 351/211, 212, 351/205, 206, 247, 246, 200

[56] References Cited

U.S. PATENT DOCUMENTS 4,572,628 2/1986 Nohda ........................... 351/212

OTHER PUBLICATIONS

William F. Long, A Matrix formalism for Decentration Problems, vol. 53, No. 1, Jan. 1976, pp. 27–33.

*Primary Examiner*—Hung X. Dang

[57] ABSTRACT

An ophthalmologic curvature measuring device measures the shape of a central portion and the shape of a peripheral portion of a curved surface such as a cornea of the eye or contact lenses. The measuring device has a small size and is capable of being hand held during measurement. A plurality of light beams are first projected onto the cornea and corneal periphery of the eye. A first projection unit then projects a first mark onto a first region of the subject eye while a second projection unit projects a pair of second marks onto a second region of the subject eye. An objective lens transmits reflected images of the first and the second marks to a measurement unit which measures the second marks at first and second timings. A displacement detecting unit then detects relative angular displacement of the measured first and second positions of the second marks about an optical axis and a calculation unit calculates the second region of the subject curved surface from the relative angular displacement detected by the displacement detecting unit.

22 Claims, 20 Drawing Sheets

OPHTHALMOLOGIC CURVATURE MEASURING DEVICE AND METHOD TO CONJOINTLY MEASURE A CENTRAL AND PERIPHERAL PORTION OF A CURVED SURFACE

CROSS-REFERENCE TO RELATED APPLICATIONS

This application is based upon and claims priority of JP Application Number 08091512 filed Apr. 12, 1996, the contents being incorporated herein by reference.

BACKGROUND OF THE INVENTION

The present invention relates to ophthalmologic devices including devices for measuring the curvature of curved surfaces. More particularly, the present invention relates to ophthalmologic devices including curvature measurement devices for manual measurement of contact lenses and the like.

With regard to surfaces in ophthalmologic devices which are to be measured, curved surfaces (i.e. "toric surfaces" hereinbelow) are defined as circular arcs which do not pass through a center of curvature when caused to rotate around an axis.

In the field of ophthalmologic devices and the like, two curvature measuring devices measure a radius of curvature in two principal diametral directions. To measure the radius of curvature, the devices project an optical index and determine curvature from a distance of the optical index to its reflected image. These devices are particularly used to measure the shape of a cornea for contact lenses.

For example, one device to detect a radius of curvature projects an annular index or three or more point light sources onto a subject surface. The device then detects the displacement of the reflected images from the index to measure curvature. U.S. Pat. No. 4,572,628 sets forth this type of representative device for measuring radii of curvature.

To determine an appropriate shape for contact lenses, shape measurement of a central portion of a cornea for a subject eye is measured. The shape of the central portion of the cornea is generally a region 3 mm in diameter. However, in order to fit contact lenses, it is necessary to know the state of the cornea in more detail. For this purpose, together with measurements of the central portion of the cornea, measurements are taken of sites about the periphery of the cornea.

There are generally two representative prior art measuring devices which can measure the shape of the peripheral portions of the cornea, namely: a first type which is independently equipped with measuring systems to measure the central portion, and a second type having an optical system which jointly measures the periphery and the central portion of the cornea.

The first type of measuring devices is equipped with measuring systems for measuring the peripheral portion and the central portion independently. This type of curvature measurement device has plural annular forms of index, and the image reflected in the cornea is captured by a CCD camera and the like for picture analysis.

The second type of curvature measurement devices, i.e. joint use types, are also known with measuring systems for the peripheral portion and the central portion of the cornea. These devices include a fixed sighting lamp which is viewed by a subject eye. By aiming the device in a direction inclined at an angle to a fixed eyeball, a portion of the corneal periphery which is to be measured is determined and the device performs measurement in a state positioned on the optical axis of the instrument. The fixed sighting lamp is movable in plural directions, up and down, and left and right to select the site of measurement. Point lamps are used for each of these sighting lamps.

In order to correspond to various subjects, measurement is first made manually. However, in the case of a device which measures manually, because there is no jaw receiver or frame to fix the instrument and the subject, the subject's face is not fixed, and measurements are carried out in a free state. Accordingly, because the relative position of the device and the subject are easily displaced, placement in a fixed predetermined relative position is difficult.

In particular, in the case of manually the peripheral portion of the cornea, a displacement in relative position of the curvature measuring device and the subject easily occur. Accordingly, in prior art curvature measuring devices of the type in which a subject views a fixed sighting lamp and the site to be measured is selected, many cases occur in which, even though the subject looks closely at the fixed sighting lamp, a definite angle cannot be precisely fixed. Thus, a disadvantage is that an unintended site is measured.

In devices of a type in which independent measurement units are disposed for peripheral portions and central portions, because there is no necessity for a subject's eye to oscillate, displacement of these measurement sites does not occur. and the device becomes large. Thus, these types of devices are not preferable for manual use.

BRIEF SUMMARY OF THE INVENTION

It is therefore an object of the present invention to solve the above problems by providing a device which performs peripheral measurement of the cornea without oscillation of a subject's eye.

It is a further object of the present invention to measure a curvature shape of a subject cornea in a manually operated state.

It is a further object of the present invention to provide a small, hand held device which measures a peripheral portion of a subject curved surface by a pair of projection optical systems.

Moreover, it is an object of the present invention to perform measurements while rotating a curvature measuring device to detect a rotation angle about an axis.

It is still a further object of the present invention to maintain precise measurement when manually rotating, an ophthalmologic measurement device itself to rotate.

It is a further object of the present invention to provide an ophthalmologic curvature measuring device which measures by hand the shape of a cornea, contact lens and the like, while measuring a central portion and peripheral portions.

Objects of the invention are achieved by an ophthalmologic curvature measuring device to measure a subject curved surface, including a first projection unit to project a first mark onto a first region of the subject curved surface; a second projection unit to project a pair of second marks onto a second region of the subject curved surface outside of the first region; an objective lens having an optical axis to transmit a reflected image of the first mark and the second marks from the first region of the subject curved surface; a measurement unit to receive the reflected image of the second marks from the objective lens, and to measure a first position of the second marks at a first timing and a second position of the second marks at a second timing different from the first timing; a displacement detecting unit to detect relative angular displacement of the measured first and second positions of the second marks about the optical axis of the objective lens; and a calculation unit to calculate the second region of the subject curved surface from the relative angular displacement detected by the displacement detecting unit.

Objects of the invention are further achieved by a curvature measurement method to measure curvature of a subject curved surface, including the steps of projecting a first group of light beams onto a first region of a subject curved surface; detecting reflected directions of the first group of light beams from the subject curved surface; determining a shape index of the subject curved surface, including a principal meridian azimuth of two principal meridian directions of the subject curved surface, and curvature of the two principal meridian directions from the reflected directions of the first group; projecting a second group of light beams onto a second region of the subject curved surface outside the first region; measuring a first reflected direction of the first light beam group and the second light beam group in the subject curved surface projected from a first azimuth about the principal axis of the subject curved surface; measuring a second reflected direction of the first light beam group and the second light beam group in the subject surface projected from a second azimuth about the principal axis of the subject curved surface; determining a shape index of the subject curved surface from the first and second reflection directions of the first light beam group; determining relative azimuth change about the principal axis of the subject curved surface from a difference of respective values of the two principal meridian directions; converting standard directions of the measurements of the relative azimuth directions into first and second reflection directions of the second light beam group; and determining curvature of the region of the subject curved surface from the first and second reflection directions.

Moreover, objects of the invention are achieved by an ophthalmologic curvature measuring device to measure a subject curved surface, including an observational optical system to observe a subject eye; and an index display unit to selectively display an index of a first or second angular position about an optical axis of the observational optical system.

BRIEF DESCRIPTION OF THE DRAWINGS

These and other objects and advantages of the invention will become apparent and more readily appreciated from the following description of the preferred embodiments, taken in conjunction with the accompanying drawings of which.

DETAILED DESCRIPTION OF THE PREFERRED EMBODIMENTS

Figure 1:
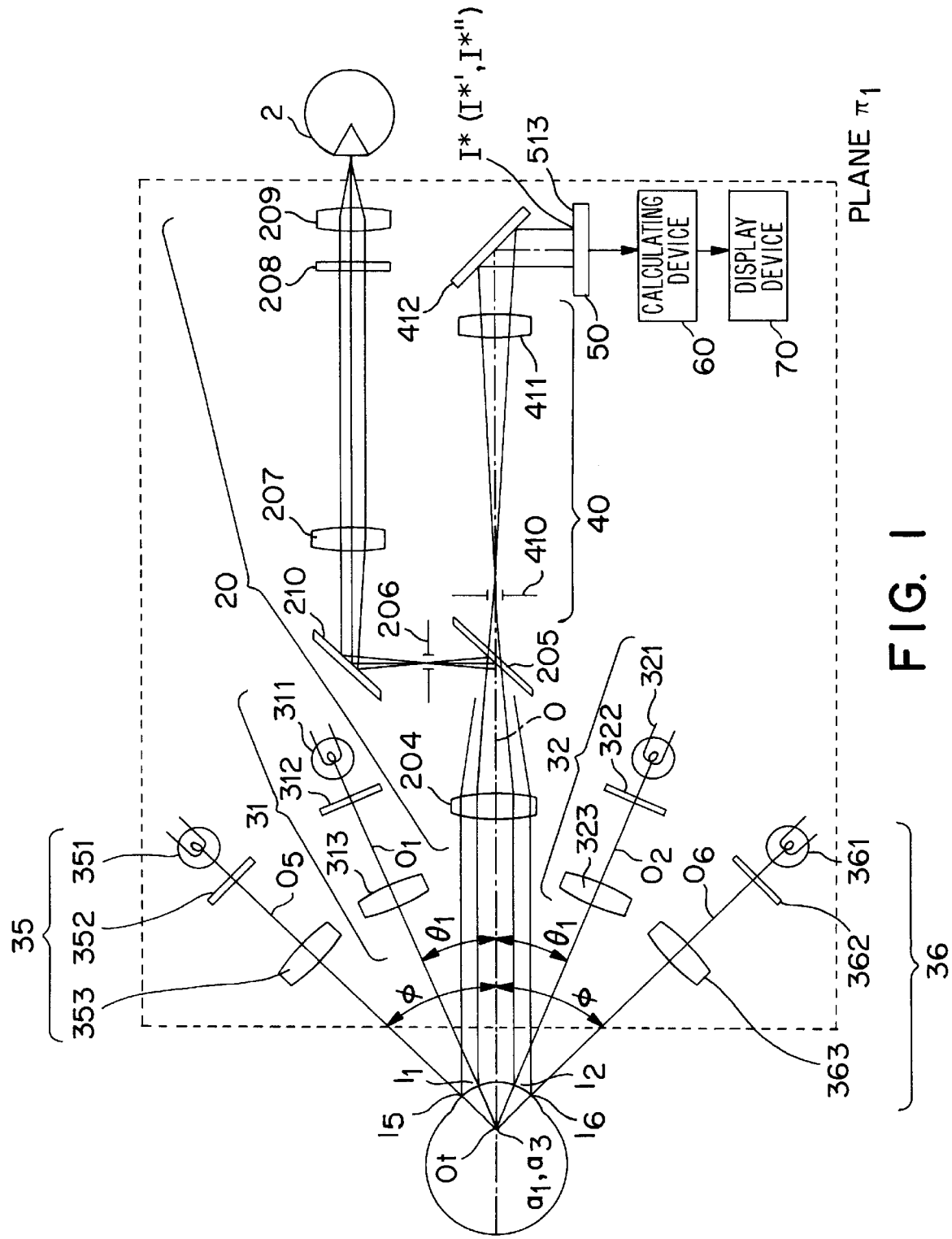
FIG. 1 is a schematic diagram of a curvature measuring device which measures an eye in a first plane according to a preferred embodiment of the present invention.

Reference will now be made in detail to the preferred embodiments of the present invention, examples of which are illustrated in the accompanying drawings, wherein like reference numerals refer to like elements throughout.

Figure 2:
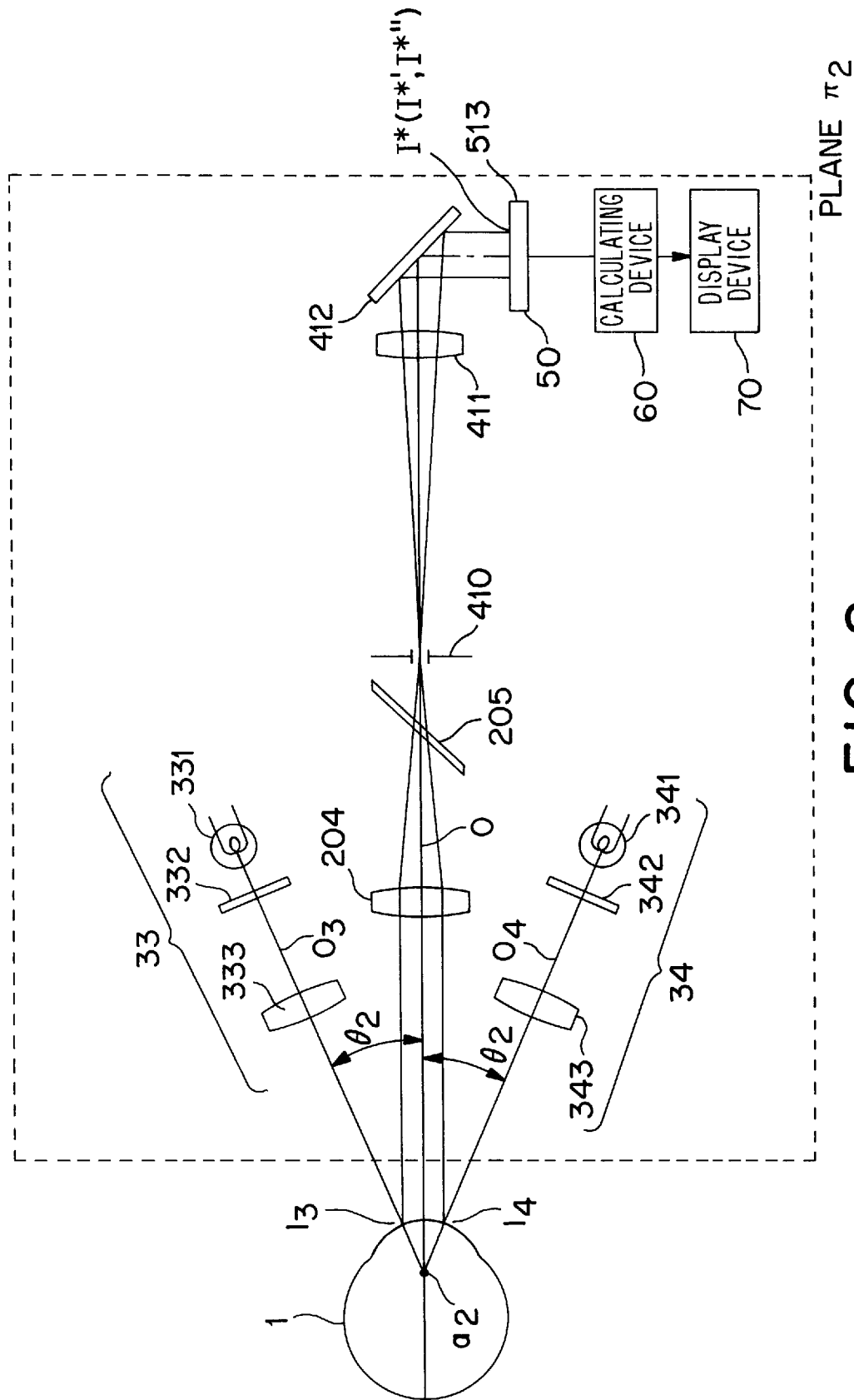
FIG. 2 is a schematic diagram of a curvature measuring device which measures an eye in a second plane according to a preferred embodiment of the present invention.

FIGS. 1 and 2 illustrate a curvature measuring device to which the present invention is applied. FIGS. 1 and 2 are illustrative diagrams showing the arrangement of an optical system of a curvature measuring device. In FIG. 1, the plane coinciding with the plane of the paper is taken as plane $\pi_1$ and in FIG. 2, the plane coinciding with the plane of the paper is taken as plane $\pi_2$. Here, the plane $\pi_1$ and the plane $\pi_2$ are mutually orthogonal planes. The light path of the optical system of the curvature measuring device is arranged along the two mutually orthogonal planes $\pi_1$ and $\pi_2$.

A description is given below relating to the arrangement of the optical systems of this curvature measuring device, and of the images which are formed by the optical systems.

Referring to FIGS. 1 and 2, the curvature measuring device of the present invention is equipped with an observation optical system 20 in order to observe the measurement site in a subject curved surface 1, and is also equipped with projection optical systems 31, 32, 33, 34, 35, 36, in order to respectively project luminous spots $I_1$, $I_2$, $I_3$, $I_4$, $I_5$, $I_6$ onto the curved surface 1. A measuring optical system 40 forms reflected images of the luminous spots $I_1$, $I_2$, $I_3$, $I_4$, $I_5$, $I_6$ which have been projected by way of the projection optical systems 31, 32, 33, 34, 35, 36. In addition, photoelectric conversion devices measure the positions of the reflected images $I_1^*$, $I_2^*$, $I_3^*$, $I_4^*$, $I_5^*$, $I_6^*$ formed in the measuring optical system, while a calculating unit performs calculations to find the shape of the subject curved surface based on the positions measured by the photoelectric conversion devices. A display device then displays the calculation result.

Here, with regard to the luminous spots which are projected onto the subject curved surface, "I" is used to indicate the index of an optical axis of an optical system which projects this luminous spot. Moreover, for the images formed of the luminous spots by the measuring optical system, the luminous spots are denoted by adding "*", such that I* is used.

As illustrated in FIG. 1, a portion of the optical system containing objective lens 204 is used in both the observation optical system 20 and the measuring optical system 40. The positional relation of the projection axes is described below, with reference to FIGS. 14 and 15A.

The projection optical systems 31, 32 illustrated in FIG. 1 have a plane $\pi_1$ including respective projection optical axes $O_1$, $O_2$ and the optical axis O (termed hereinbelow the "main optical axis") of objective lens 204. Also, the respective projection optical axes $O_1$, $O_2$ form an angle $\theta_1$ with the main optical axis O and are arranged to intersect at a point $a_1$ on the main optical axis O. At this time, taking a plane $\pi_3$ orthogonal to the main optical axis O as a projection standard plane, the point of intersection of the main optical axis O and the projection standard plane is taken as a projection standard point O†. The plane $\pi_3$ is orthogonal to the previously mentioned planes $\pi_1$ and $\pi_2$. Moreover, the direction to the light source from the projection standard point O† (FIG. 15A), with regard to the projection on the projection standard plane as a direction of projection and the direction of projection of the projection optical system, is taken as the projection standard direction.

The projection optical systems 33, 34 illustrated in FIG. 2 have, in a plane $\pi_2$ orthogonal to the plane $\pi_1$, respective projection optical axes $O_3$, $O_4$ including the main optical axis. The respective projection optical axes $O_3$, $O_4$ form an angle $\theta_2$ with the main optical axis O and are arranged to intersect at point $a_2$ on the main optical axis O.

Figure 3:
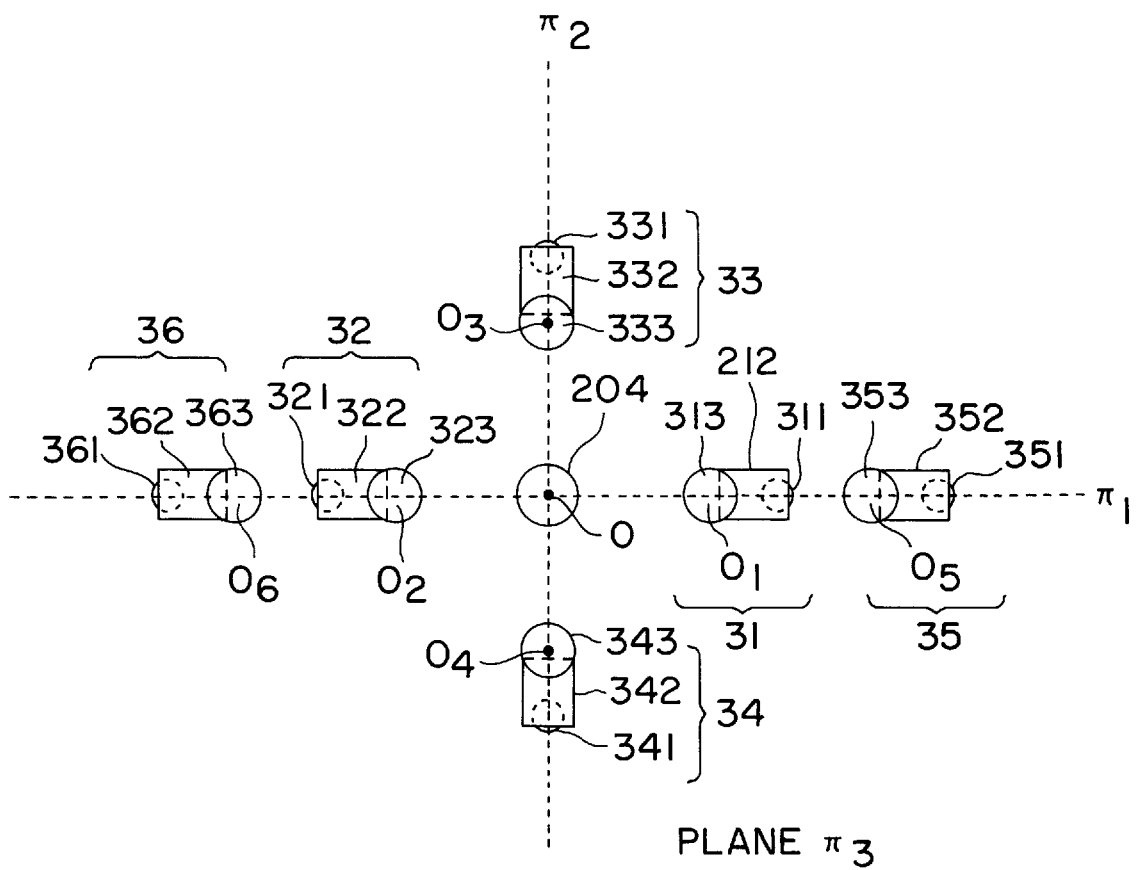
FIG. 3 is a schematic diagram of a curvature measuring device in a third plane as viewed from a subject curved surface side according to a preferred embodiment of the present invention.

As illustrated in FIG. 3, the projection optical systems 35, 36 have in the plane $\pi_1$ the respective projection optical axes $O_5$, $O_6$, including the main axis O. As illustrated in FIG. 1, the respective projection axes $O_5$, $O_6$ respectively make an angle $\phi$ with the main optical axis O and are arranged to intersect at a point $a_3$ on the main axis O.

Here, with regard to the magnitudes of the angles $\theta_1$, $\theta_2$, $\phi$, the angle $\phi$ is greater than either of $\theta_1$ and $\theta_2$. Further, a normal line at a point where the luminous spots $I_1$, $I_2$, $I_3$, $I_4$, $I_5$, $I_6$ are projected is selected at a double magnitude of the angle formed with the main optical axis O.

Moreover, when the above-mentioned curved surface 1 is a portion of a spherical surface, the points $a_1$, $a_2$, $a_3$ are selected at the same points on the main optical axis O and the angles $\theta_1$, $\theta_2$, are selected in an equivalent magnitude. Accordingly, luminous spots $I_1$, $I_2$, $I_3$, $I_4$, are in a region projected in the curved surface 1 by way of the projection optical systems 31, 32, 33, 34, and the luminous spots $I_5$, $I_6$ are respectively projected outside of the region in the curved surface 1 by the projection optical systems 35, 36.

Moreover, the projection optical systems 31, 32, 33, 32, 35, 36 have, respectively on the respective optical axes $O_1$, $O_2$, $O_3$, $O_4$, $O_5$, $O_6$, illuminating light sources 311, 321, 331, 341, 351, 361, respective pinhole plates 312, 322, 332, 342, 352, 362, and respective collimator optical systems 313, 323, 333, 343, 353, 363.

The light path of the observation optical system 20 and the measuring optical signal 40, at least in a more rearward direction than the objective lens 204, is branched by way of the beam splitter 205 into a measuring optical path and an observation optical path. The objective lens 204 of observation optical system 20 is common to the above-mentioned measuring optical path and observation optical path.

On one of the optical paths branched by the beam splitter 205, a re-imaging lens 207 is disposed on an observation optical path reflected by beam splitter 205. Re-imaging lens 207, together with objective lens 204, forms a telocentric optical system. Stop 206 is disposed in a plane which coincides with the rear side focal plane of objective lens 204 and a front side focal plane of re-imaging lens 207. A reflected image I* of a mark on the subject curved surface 1 is formed on the focal plane 208, objective lens 204, and re-imaging lens 207. This reflected image I* is observed by observer 2 via eyepiece lens 209.

On the other optical measurement beam path branched by the beam splitter 205, a telocentric optical system is formed from stop 410, re-imaging lens 411, and objective lens 204. Similarly to the above-mentioned observation beam path, a stop 410 is disposed in a plane which coincides with the rear side focal plane of the objective lens 204 and the front side focal plane of the re-imaging lens 411. By making stop 411 sufficiently small, a light beam can be selected which is parallel to the main optical axis O.

The optical axis from the re-imaging lens 411 is deflected by mirror 412, and is incident on the photoelectrical converter 50. The photoelectrical converter 50 has its light receiving surface 513 arranged such that the light deflected by the mirror 412 becomes perpendicular to the optical axis O.

Figure 14:
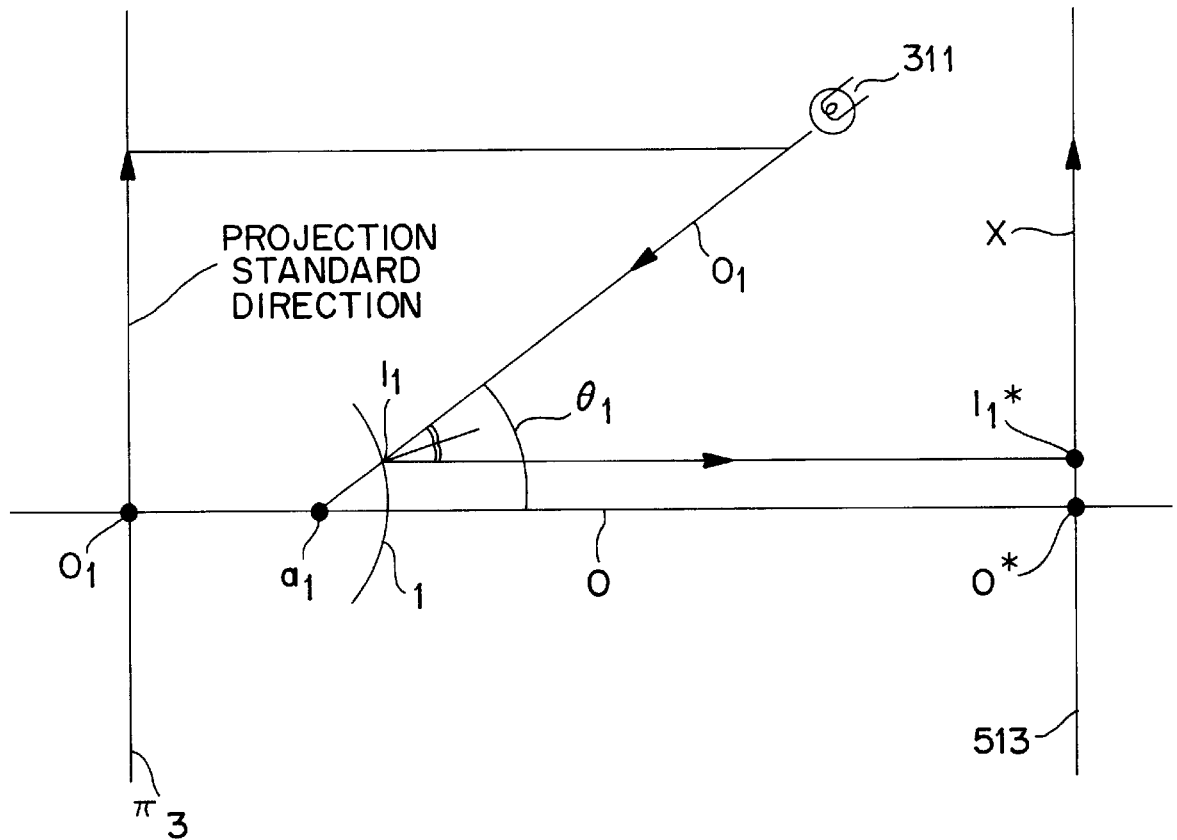
FIG. 14 is a schematic diagram defining a projection standard surface and an image standard surface.
Figure 15A:
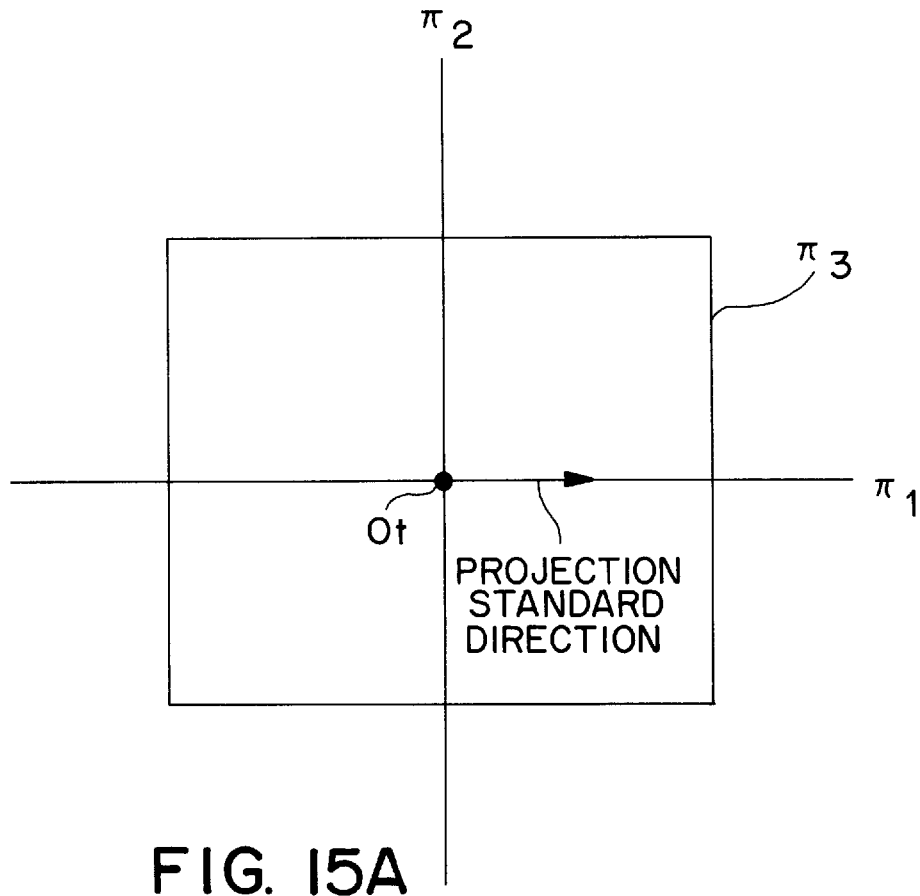
FIG. 15A is a schematic diagram defining a projection standard direction in a projection standard surface according to a preferred embodiment of the present invention.
Figure 15B:
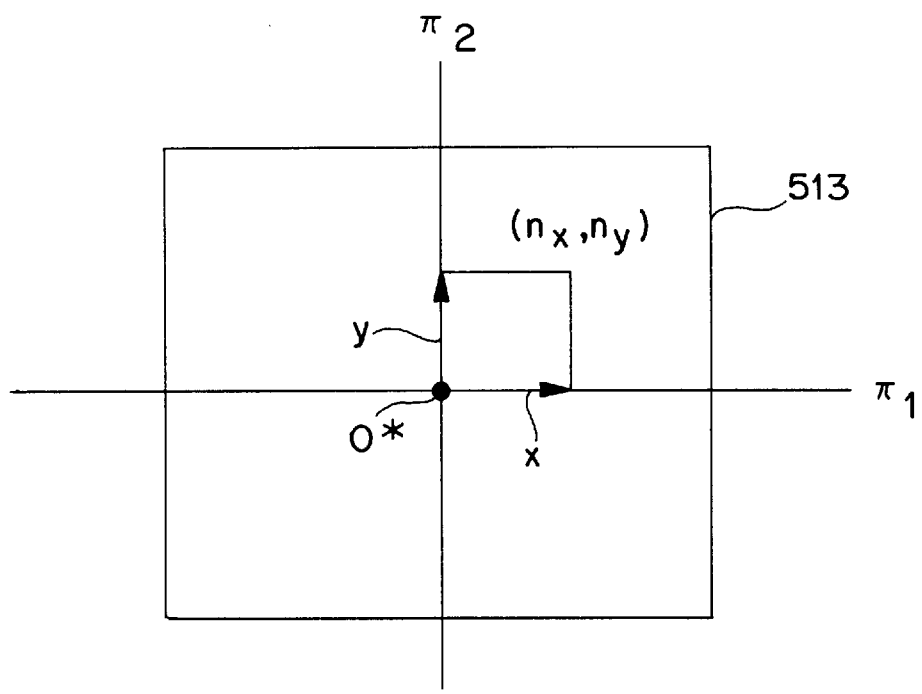
FIG. 15B is a schematic diagram defining a projection standard direction in an image standard surface.

In FIGS. 14 and 15B, the intersection point of the optical axis O and the light receiving surface 513 is taken as the standard point O*. Moreover, on the light receiving surface 513, the direction which corresponds to the projection standard direction, with the standard point O* as the starting point, is taken as the image standard direction x. The direction y is taken as a direction at a right angle to image standard direction x. The reflected images $I_1^*, I_2^*, I_3^*, I_4^*, I_5^*, I_6^*$ are reflected by subject curved surface 1 in light receiving surface 513.

Next, a description is given regarding the positions of images I* formed on the light receiving surface 513 by the measuring optical system, and the positions of the respective projected luminous spots I on the subject curved surface 1 due to the projection optical systems 31, 32, 33, 34, 35, 36. In the measurement of the subject curved surface 1 in the curvature measuring device, the main optical axis O of the curvature measuring device is measured in a state which passes through the center of the subject curved surface 1. In particular, the main optical axis O is measured to determine the measurements of toric and similar aspheric surfaces. Furthermore, the aforementioned main optical axis O is measured in a state including a surface which contains either of the major diameters of the subject curved surface.

A description is now given of a case in which the subject curved surface is spherical. In the spherical case, the direction joining the images $I_1^*, I_2^*$, the direction joining the images $I_3^*, I_4^*$, and the direction joining the images $I_5^*, I_6^*$, are respectively constant. Namely, the angles (termed hereinbelow "projection directions") with respect to the projection standard direction of each projection direction of the projection optical systems 31, 32, 33, 34, 35, 36, and the directions (termed hereinbelow "image directions") of the images $I_1^*, I_2^*, I_3^*, I_4^*, I_5^*, I_6^*$ of the respective image standard point O*, are respectively equivalent. Accordingly, if $\pi_1$ and $\pi_2$ are orthogonal, each image direction of the images $I_1^*, I_2^*, I_4^*, I_6^*$ are respectively orthogonal to each image direction of the images $I_3^*, I_5^*$.

Moreover, the intervals of the respective image standard points O* of the images $I_1^*, I_2^*, I_3^*, I_4^*$ are equivalent, and the intervals of the respective image standard points O* of the images $I_5^*, I_6^*$ are equivalent. When the radius of curvature of the curved surface 1 increases and decreases, the interval of the respective images $I_1^*, I_2^*, I_3^*, I_4^*, I_5^*, I_6^*$ and the image standard points O* increase and decrease corresponding to the changes in the radius of curvature of the subject curved surface 1.

Moreover, according to the radius of curvature of the subject curved surface 1, the respective intervals of the images $I_1^*, I_2^*$ and the image standard point O*, and the respective intervals of the images $I_5^*, I_6^*$ and the image standard point O*, are small.

Next, a description is given of a case when the subject curved surface 1 is a portion of a toric surface, and when one of the main meridians (termed hereinbelow the "first main meridian") $L_1$ is in the plane $\pi_1$. At this time, in the toric surface, the two main meridians are orthogonal, the other main meridian (termed hereinbelow the "second main meridian") $L_2$ is in the plane $\pi_2$.

The direction joining the images $I_1^*, I_2^*$, and the direction joining the images $I_3^*, I_4^*$, and the direction joining the images $I_5^*, I_6^*$, are respectively constant. Namely, the angles (termed hereinbelow "projection directions") with respect to the projection standard direction of each projection direction of the projection optical systems 31, 32, 33, 34, 35, 36, and the directions (termed hereinbelow "image directions") of the images $I_1^*, I_2^*, I_3^*, I_4^*, I_5^*, I_6^*$ of the respective image standard point O*, are respectively equivalent. Accordingly, in a case that the subject curved surface is spherical, each image direction of the images $I_1^*, I_2^*, I_3^*, I_4^*, I_5^*, I_6^*$, and each image direction of the images $I_1^*, I_2^*, I_3^*, I_4^*, I_5^*, I_6^*$ in this condition, coincide.

Figure 3A:
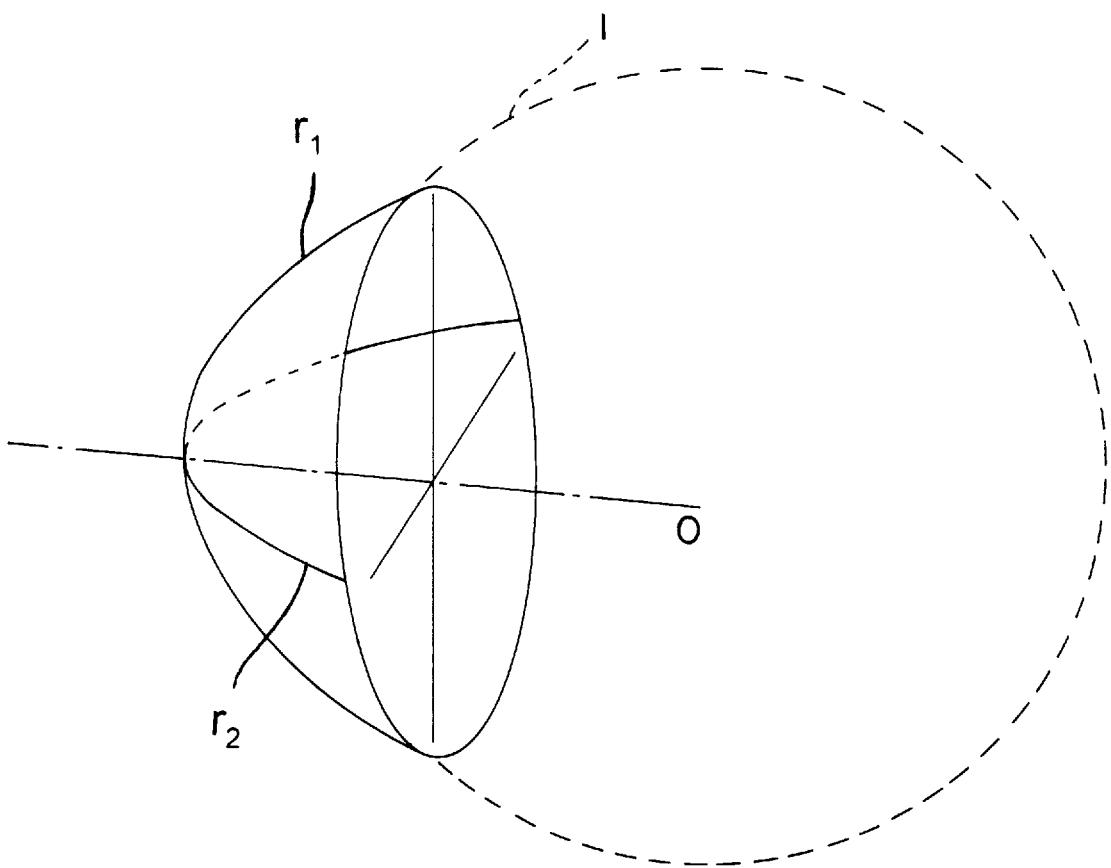
FIG. 3A is a three dimensional diagram of the eye illustrated in FIG. 1.

FIG. 3A is a three dimensional representation of the curved surface 1 (e.g., an eye) illustrated in FIG. 1. When a radius of curvature $r_1$, (hereinbelow termed a "first main radius of curvature") of a direction of a first main meridian $L_1$, is greater than a radius of curvature $r_2$ (hereinbelow termed a "second main radius of curvature") of a direction of a second main meridian $L_2$, the intervals of the images $I_1^*, I_2^*$ and the image standard point O* are respectively greater than the intervals of the images $I_3^*, I_4^*$ and the image standard point O*. When the first main radius of curvature $r_1$ is smaller than the second main radius of curvature $r_2$, the intervals of the images $I_1^*, I_2^*$ and the image standard point O*, are respectively smaller than the intervals of the images $I_3^*, I_4^*$ and the image standard point O*; and each interval of the images $I_1^*, I_2^*, I_3^*, I_4^*, I_5^*, I_6^*$ of the respective image standard point O*, corresponds to each main radius of curvature.

Next, a description is given of the case in which the subject curved surface 1 is a portion of a toric surface, and also, either of the two main meridians $L_1, L_2$ is not in a plane of either of the planes $\pi_1, \pi_2$. Here, the direction of either one of the main meridians $L_1$, makes an angle $\alpha$ to the plane $\pi_1$. At this time, due to the orthogonality of main meridians $L_1$ and $L_2$ and of $\pi_1$ and $\pi_2$, main meridian $L_2$ also makes an angle $\alpha$, to the plane $\pi_2$. Moreover, the case is such that the curvature $r_1$ of the direction of one main meridian $L_1$ is smaller than the main radius of curvature $r_2$ of the direction of the other main meridian $L_2$.

Each position of the images $I_1^*, I_2^*, I_3^*, I_4^*, I_5^*, I_6^*$ is respectively close to a meridian whose radius of curvature becomes a minimum. Namely, each position becomes compressed such that it approaches the direction L* on the light receiving surface 513 corresponding to the direction of the main meridian $L_1$. Accordingly, the image direction of respective images, in the case that the subject curved surface 1 is a portion of a spherical surface, directions arise which have been displaced from the respective image directions. Also, the interval of the respective images and the image standard point O* respectively corresponds to the curvature at the projected site of the luminous spots $I_1, I_2, I_3, I_4, I_5, I_6$ of the subject curved surface 1.

Next, photoelectrical converter 50 is described. For an image which has been formed on light receiving surface 513 of a luminous spot, a projected distance in the image standard direction x of the interval, of the image standard point O* and the image I* is output as $\eta_x$, and the projected distance in the image standard direction y, which is at a right angle to the image standard direction x on the light receiving surface 513, of the interval of the image standard point O* and the image I*, is output as $\eta_y$. Namely, respectively corresponding to the images $I_1^*, I_2^*, I_3^*, I_4^*, I_5^*, I_6^*$ each projected distance in the x and y directions, $(\eta_{x1}, \eta_{y1})$, $(\eta_{x2}, \eta_{y2})$, $(\eta_{x3}, \eta_{y3})$, $(\eta_{x4}, \eta_{y4})$, $(\eta_{x5}, \eta_{y5})$, $(\eta_{x6}, \eta_{y6})$, is output.

First, a case will be described in which a relative angular displacement of 90° is made with respect to a subject curved surface 1 between a first timing and a second timing.

In the case that, between the present device and the subject curved surface 1, a relative angular displacement of 90° is made around the main optical axis, respectively by way of the projection optical systems 31, 32, 33, 34, 35, 36, luminous spots $I_1', I_2', I_3', I_4', I_5', I_6'$, are respectively projected onto the subject curved surface 1. By way of the measuring optical system 40, the respective images $I_1', I_2', I_3', I_4', I_5', I_6'$, of these luminous spots $I_1', I_2', I_3', I_4', I_5', I_6'$ projected onto the subject curved surface 1 are respectively formed on the light receiving surface 513 of photoelectrical converter 50.

In the photoelectrical converter 50, similar to the images $I^{*'}$ of the luminous points formed on the light receiving surface 513, the projected distance in the image standard direction x of the interval between the image standard point $O^*$ and the images $I^{*'}$ is output as $\eta_x'$, and the projected distance in the image standard direction y, which is at right angles to the image standard direction x on the light receiving surface 513, is output as $\eta_y'$. Namely, respectively corresponding to the images $I_1^{*'}$, $I_2^{*'}$, $I_3^{*'}$, $I_4^{*'}$, $I_5^{*'}$, $I_6^{*'}$, each projected distance in the x and y directions, $I_1''$, $I_2''$, $I_3''$, $I_4''$, $I_5''$, $I_6''$, is output.

Next, a description is given of the data process in the calculating device 60. The calculating device 60, based on the interval of the images $I_1^*$ and $I_2^*$, each projected distance $h_1$ and $\Delta_1$ in the x and y directions, the interval of the images $I_3^*$ and $I_4^*$, the projected distance $h_2$ in the x direction, the interval of the images $I_5^*$ and $I_6^*$, the projected distances $h_3$ and $\Delta_2$ in the x and y directions, the interval of the images $I_1'^* I_2'^*$, each projected distance $h_1'$ and $\Delta_2'$ in the x and y directions, the interval of the images $I_3'^*$ and $I_4'^*$, the projected distance $h_2'$ in the x direction, the interval of the images $I_5'^*$ and $I_6'^*$, the projected distances $h_3'$ and $\Delta_2'$ in the x and y directions, performs calculations to find the shape of the subject curved surface 1.

Namely, the calculating device 60, based on $h_1$, $h_2$, and $\Delta_1$, for the regions in which the luminous spots $I_1$, $I_2$, $I_3$, $I_4$ are projected, performs calculations to find the two main meridian directions and the curvature of each meridian direction, and, based on $h_1'$, $h_2'$, and $\Delta_1'$, for the regions in which the luminous spots $I_1'$, $I_2'$, $I_3'$, $I_4'$ are projected, performs calculations to find the two main meridian directions and the curvature of each main meridian direction. The calculating device 60 furthermore, based on $h_3$, $\Delta_2$, $h_3'$, for the regions in which the luminous spots $I_5$, $I_6$, $I_5'$, $I_6'$ are projected, performs calculations to find the two main meridian directions and the curvature of each main meridian direction. A detailed description of these calculations is given hereinbelow.

First, in the first timing, by way of the $(\eta_{x1},\eta_{y1})$, $(\eta_{x2},\eta_{y2})$, $(\eta_{x3}, \eta_{y3})$, $(\eta_{x4}, \eta_{y4})$, $(\eta_{x5}, \eta_{y5})$, $(\eta_{x6}, \eta_{y6})$, output from the photoelectrical converter 50, the above-mentioned $h_1$, $h_2$, $h_3$, $\Delta_1$, $\Delta_2$ are written in Equation (1):

$$h_1 = \eta_{x1} + \eta_{x2}$$
$$\Delta_1 = \eta_{y1} + \eta_{y2}$$
$$h_2 = \eta_{x3} + \eta_{y4}$$
$$h_3 = \eta_{x5} + \eta_{x6}$$
$$\Delta_2 = \eta_{y5} + \eta_{y6} \qquad (1)$$

Moreover, the above-mentioned $(\eta_{x1}',\eta_{y1}')$, $(\eta_{x2}',\eta_{y2}')$, $(\eta_{x3}', \eta_{y3}')$, $(\eta_{x4}', \eta_{y4}')$, $(\eta_{x5}', \eta_{y5}')$, $(\eta_{x6}', \eta_{y6}')$ are output, and the above-mentioned $h_1'$, $h_2'$, $h_3'$, $\Delta_1'$, $\Delta_2'$ are written in Equation (2):

$$h_1' = \eta_{x1}' + \eta_{x2}'$$
$$\Delta_1' = \eta_{y1}' + \eta_{y2}'$$
$$h_2' = \eta_{x3}' + \eta_{y4}'$$
$$h_3' = \eta_{x5}' + \eta_{x6}'$$
$$\Delta_2' = \eta_{y5}' + \eta_{y6}' \qquad (2)$$

In geometrical optics, the refractive action in a toric surface can be considered as separated into refractive action due to a spherical surface, as a standard, and refractive action due to a cylindrical surface. Namely, the refractive action of reflection in a toric surface, because the refractive power differs according to the azimuth angle of a meridian, a fixed refractive power, and a variable portion of refractive power due to the meridian are considered separately. Consequently, reflection in a toric surface can be considered as a combination of refractive power which is not dependent on the azimuth angle of a meridian, corresponding to the refractive action of reflection in a spherical surface, and a variable portion of the refractive power due to the meridian, corresponding to the refractive action in a cylindrical surface.

Figure 4:
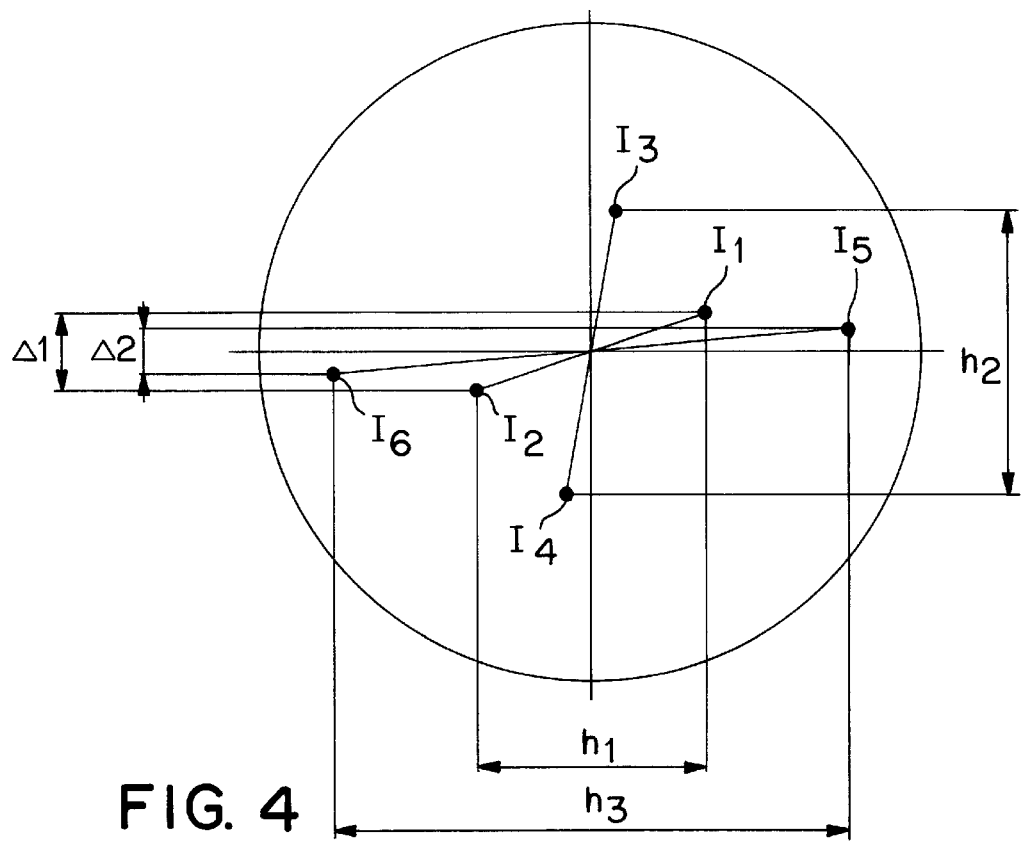
FIG. 4 is a schematic diagram of luminous spots projected onto a subject curved surface in a first timing measurement by a curvature measuring device according to a preferred embodiment of the present invention.

As illustrated in FIG. 4, the subject curved surface 1 is a portion of a toric surface. When one of the main meridians $L_1$ is in the plane $\pi_1$, the projected distances $H_1$, $H_2$, $H_3$ are defined according to the projected distances $h_1$, $h_2$, $h_3$ in Equation (3):

$$H_1 \equiv h_1$$
$$H_2 \equiv h_2$$
$$H_3 \equiv h_3 \qquad (3)$$

These projected distances $H_1$, $H_2$, $H_3$, as above-mentioned, respectively correspond to the radii of curvature in the respective directions of the meridians. FIG. 4 illustrates the projected distances $H_1$, $H_2$, $H_3$ according to a first timing.

Figure 5:
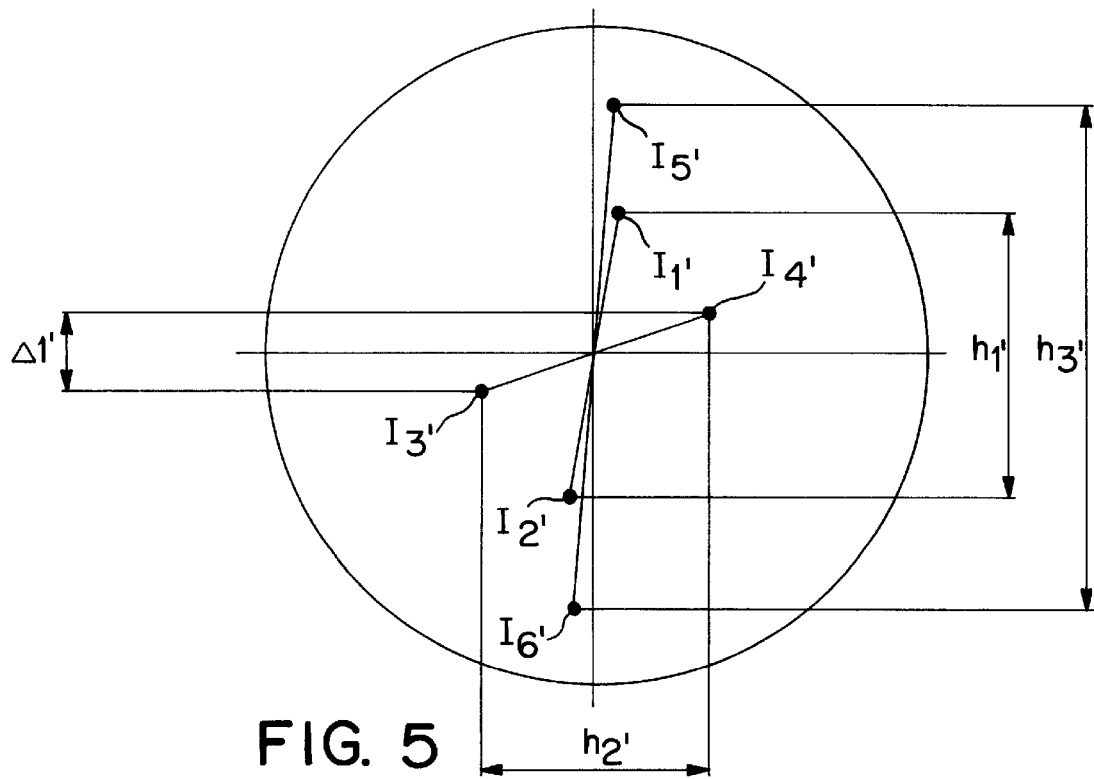
FIG. 5 is a schematic diagram of luminous spots projected onto a subject curved surface in a second timing measurement by a curvature measuring device according to a preferred embodiment of the present invention.
Figure 6:
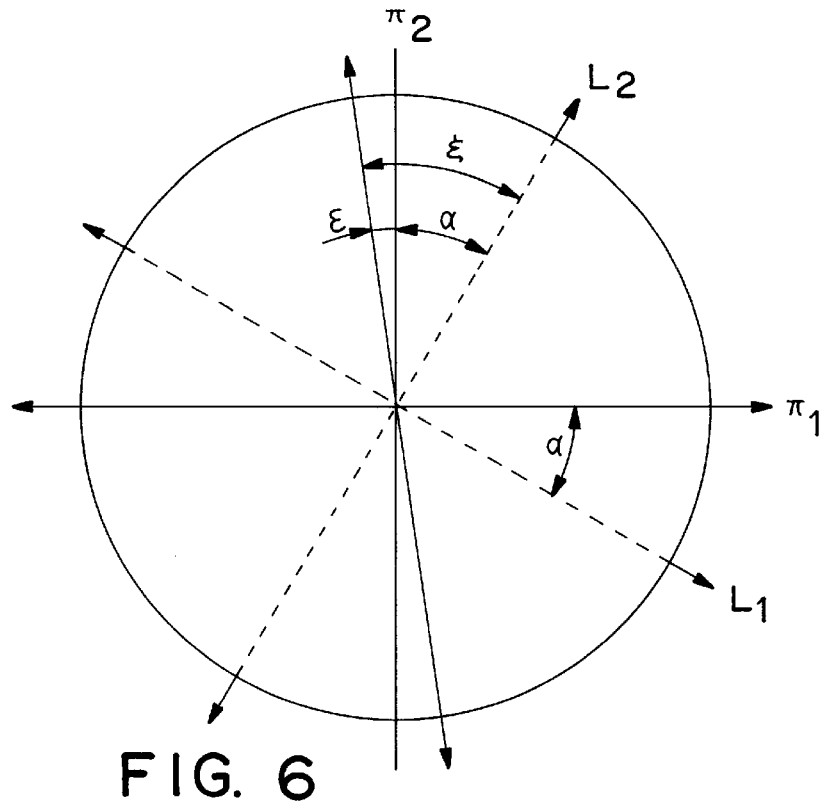
FIG. 6 is a schematic diagram of a positional relationship of a toric curved surface and a curvature measuring device according to a preferred embodiment of the present invention.
Figure 7:
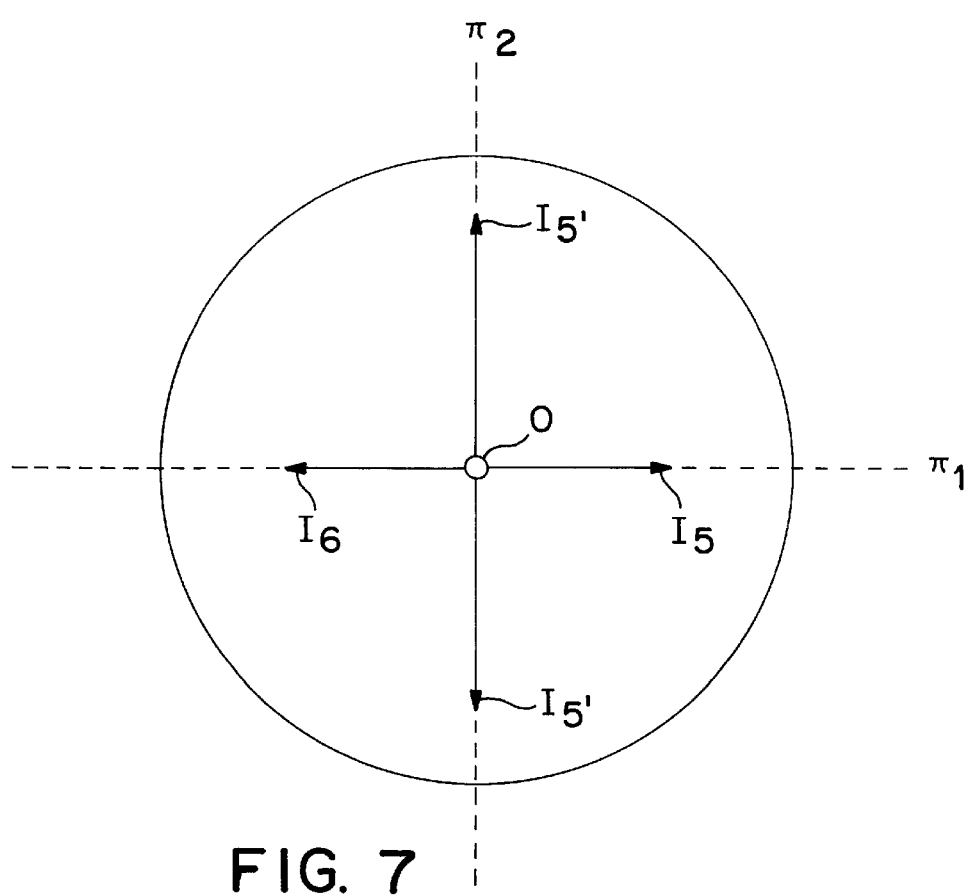
FIG. 7 is a schematic diagram of reflected images of an optical index when a subject curved surface is spherical according to a preferred embodiment of the present invention.
Figure 8:
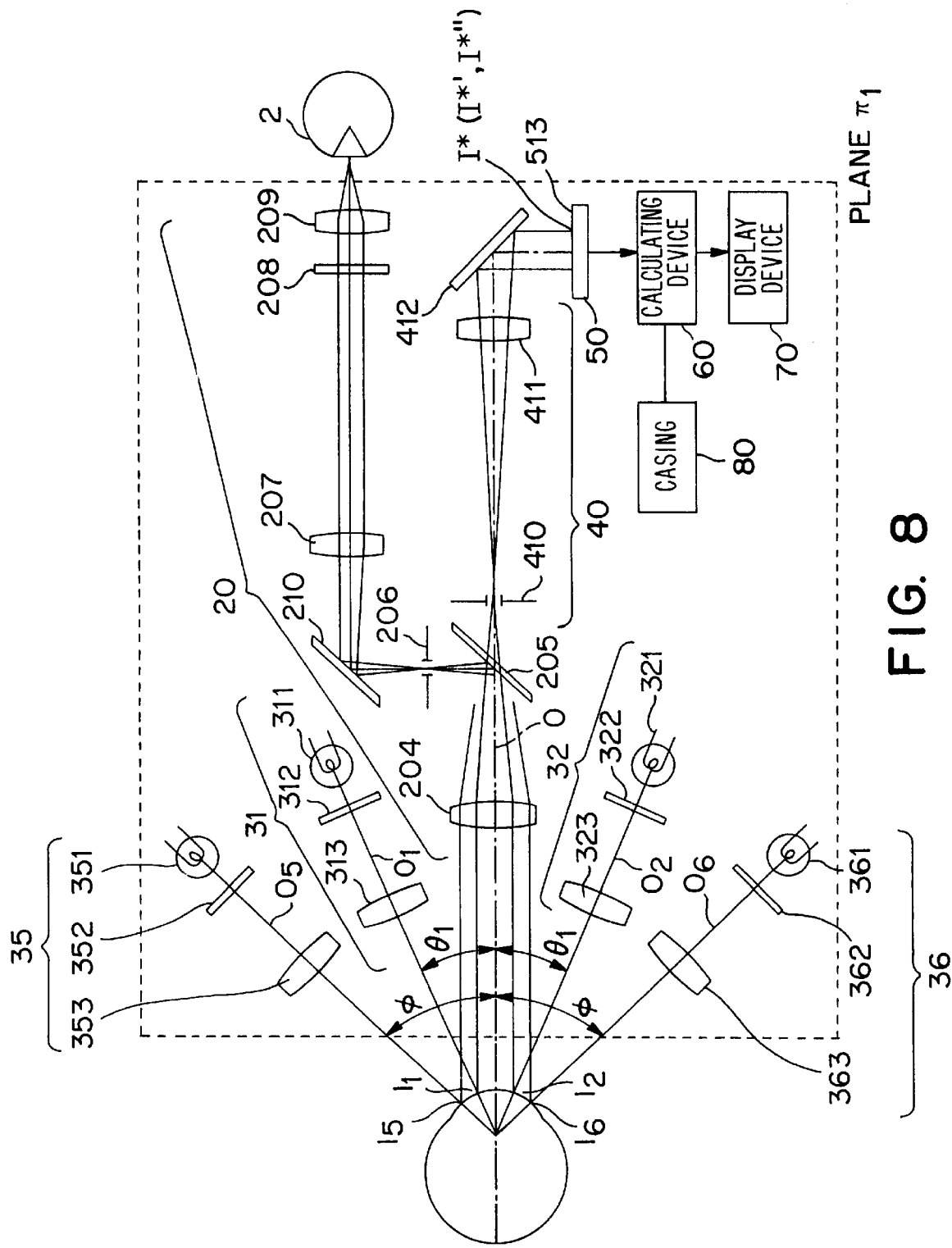
FIG. 8 is a schematic diagram of a curvature measuring device equipped with an angle sensor according to a preferred embodiment of the present invention.

Similarly, FIG. 5 illustrates a second timing which has made a relative angular displacement of 90° with respect to the subject curved surface 1, when the first main meridian $L_1$ is in the plane $\pi_2$, by way of the projected distances $h_1'$, $h_2'$, $h_3'$, the projected distances $H_1'$, $H_2'$, $H_3'$ are set forth in Equation (4):

$$H_1' \equiv h_1'$$
$$H_2' \equiv h_2'$$
$$H_3' \equiv h_3' \qquad (4)$$

As in FIG. 3 and FIG. 4, the case is described here in which the direction of any one main meridian $L_1$ makes an angle $\alpha$ to the plane $\pi_1$. By way of $H_1$, $H_2$, and $\alpha$, the quantities $h_1$, $h_2$, $\Delta_1$ become as represented by Equations (5), (6) and (7):

$$h_1 = H_2 + (H_1 - H_2)\cos^2\alpha \qquad (5)$$
$$h_2 = H_2 + (H_1 - H_2)\sin^2\alpha \qquad (6)$$
$$\Delta_1 = (H_1 - H_2)\sin\alpha \cdot \cos\alpha \qquad (7)$$

In these equations, $H_2$ corresponds to a spherical surface frequency component, and $(H_1-H_2)$ corresponds to the cylindrical frequency component only.

Equations (5), (6) and (7) are easily derived from a known refractive power matrix, as given in "A Matrix Formalism for Decentration Problems", Journal of Optometry and Physiological Optics, Vol. 53, No. 1, pp. 27–33, published in January, 1976.

Then, the values of $H_1$, $H_2$ and $\alpha$ from the above-mentioned (5), (6), (7) may be determined from Equations (8), (9), and (10):

$$H_1 = \frac{h_1 + h_2 + \sqrt{(h_1 - h_2)^2 + (2\Delta_1)^2}}{2} \qquad (8)$$

$$H_2 = \frac{h_1 + h_2 - \sqrt{(h_1 - h_2)^2 + (2\Delta_1)^2}}{2} \qquad (9)$$

$$\alpha = \frac{1}{2} \arcsin \frac{2\Delta_1}{|H_1 - H_2|} \qquad (10)$$

With respect to a normal line in the reflection surface, because the angle forming the angle of incidence, and the angle forming the exit angle, are equivalent, setting $r_1$, $r_2$ for the radius of curvature along main meridians $L_1$, $L_2$ (termed hereinbelow "main radii of curvature"), when the magnification of the measuring optical system is $\beta$, the projection optical axes $O_1$, $O_2$ form an angle $\theta_1$ with the main optical axis O, and, the projection optical axes $O_3$, $O_4$ form an angle $\theta_2$ with the main optical axis O, the interval $H_1$ of the images $I_1^*$, $I_2^*$ in the light receiving plane 513 of the reflected light parallel to the main optical axis O, and the interval $H_2$ of the images $I_1^*$, $I_2^*$, are related by Equation (11):

$$H_1 = 2\beta r_1 \sin \theta_1/2$$

$$H_2 = 2\beta r_2 \sin \theta_2/2 \qquad (11)$$

Consequently, by the above-mentioned Equations (8), (9) and (10), the main radii of curvature $r_1$, $r_2$, are given by an angle $\alpha$ formed between the direction of the first main meridian and the projection standard direction, as follows in Equation (12):

$$r_1 = \frac{1}{2\beta \sin \frac{\theta_1}{2}} \cdot \frac{h_1 + h_2 + \sqrt{(h_1 - h_2)^2 + (2\Delta_1)^2}}{2} \qquad (12)$$

$$r_2 = \frac{1}{2\beta \sin \frac{\theta_2}{2}} \cdot \frac{h_1 + h_2 - \sqrt{(h_1 - h_2)^2 + (2\Delta_1)^2}}{2} \qquad (13)$$

$$\alpha = \frac{1}{2} \arcsin \frac{2\Delta_1}{\sqrt{(h_1 - h_2)^2 + (2\Delta_1)^2}} \qquad (14)$$

Moreover, similarly, by way of $H_1'$, $H_2'$, and $\alpha$, $h_1'$, $h_2'$ and $\Delta_1'$ are represented by:

$$h_1' = H_2' + (H_1' - H_2')\cos^2\alpha \qquad (15)$$

$$h_2' = H_2' + (H_1' - H_2')\sin^2\alpha \qquad (16)$$

$$\Delta_1' = (H_1' - H_2')\sin \alpha \cdot \cos \alpha \qquad (17)$$

From Equations (15), (16), (17), $H_1'$, $H_2'$, and $\alpha$ are represented by:

$$H_1' = \frac{h_1' + h_2' + \sqrt{(h_1' - h_2')^2 + (2\Delta_1')^2}}{2} \qquad (18)$$

$$H_2' = \frac{h_1' + h_2' - \sqrt{(h_1' - h_2')^2 + (2\Delta_1')^2}}{2} \qquad (19)$$

$$\alpha = \frac{1}{2} \arcsin \frac{2\Delta_1'}{|H_1 - H_2|} \qquad (20)$$

Here, the main meridian $L_1$ is in the plane $\pi_2$, and the main meridian $L_2$ is in the plane $\pi_1$; by writing $H_1'$ and $H_2'$ as:

$$H_1' = 2\beta r_2 \sin \theta_1/2$$

$$H_2' = 2\beta r_1 \sin \theta_2/2 \qquad (21)$$

The main radii of curvature $r_1$, $r_2$ of the subject curved surface 1, and the angle $\alpha$ between the first main meridian direction and the projection standard direction, are as follows:

$$r_1 = \frac{1}{2\beta \sin \frac{\theta_2}{2}} \cdot \frac{h_1' + h_2' + \sqrt{(h_1' - h_2')^2 + (2\Delta_1')^2}}{2} \qquad (22)$$

$$r_2 = \frac{1}{2\beta \sin \frac{\theta_1}{2}} \cdot \frac{h_1' + h_2' + \sqrt{(h_1' + h_2')^2 + (2\Delta_1')^2}}{2} \qquad (23)$$

$$\alpha = \frac{1}{2} \arcsin \frac{2\Delta_1'}{\sqrt{(h_1' - h_2')^2 + (2\Delta_1')^2}} + \frac{\pi}{2} \qquad (24)$$

Next, a description is given of the regions in which the luminous spots $I_5$, $I_6$, and the luminous spots $I_5'$, $I_6'$ of the subject curved surface 1 are projected. The subject curved surface 1, the regions in which the luminous spots $I_5$, $I_6$, and the luminous spots $I_5'$, $I_6'$ are projected are central sites where luminous spots $I_1$, $I_2$, $I_3$, $I_4$ are projected, and peripheral sites where luminous spots $I_1'$, $I_2'$, $I_3'$, $I_4'$ are projected are aspheric surfaces which respectively and independently have main meridian directions and main radii of curvature. Consequently, the luminous spots $I_5$, $I_6$, and the luminous spots $I_5'$, $I_6'$, are projected in peripheral sites as two main meridian directions $\Lambda_1$, $\Lambda_2$ of the subject curved surface 1, the respective main radii of curvature as $\rho_1$, $\rho_2$ of the main meridian directions of this region, the main meridian direction $\Lambda_1$ forming an angle $\gamma$ with the plane $\pi_1$, are defined independently of the central site. Nevertheless, because $h_3$, $h_3'$, and $\Delta_2$, by way of $H_3$, $H_3'$, and $\gamma$, are represented by:

$$h_3 = H_3' + (H_3 - H_3')\cos^2\gamma \qquad (25)$$

$$h_3' = H_3' - (H_3 - H_3')\sin^2\gamma \qquad (26)$$

$$\Delta_2 = (H_3 - H_3')\sin \gamma \cos \gamma \qquad (27)$$

by way of Equations (25), (26), and (27), $H_3$, $H_3'$, and $\gamma$ are:

$$H_3 = \frac{h_3 + h_3' + \sqrt{(h_3 - h_3')^2 + (2\Delta_2)^2}}{2} \qquad (28)$$

$$H_3' = \frac{h_3 + h_3' - \sqrt{(h_3 - h_3')^2 + (2\Delta_2)^2}}{2} \qquad (29)$$

$$\gamma = \frac{1}{2} \arcsin \frac{2\Delta_2}{|H_3 - H_3'|} \qquad (30)$$

Here, from the linking relationship in reflection, because $$H_3 = 2\beta\rho_1 \sin \phi/2$$

$$H_3' = 2\beta\rho_2 \sin \phi/2 \qquad (31)$$

there are found:

$$\rho_1 = \frac{1}{2\beta \sin \frac{\phi}{2}} \cdot \frac{h_3 + h_3' - \sqrt{(h_3 - h_3')^2 + (2\Delta_2)^2}}{2} \qquad (32)$$

-continued $$\rho_2 = \frac{1}{2\beta\sin\frac{\phi}{2}} \frac{h_3 + h'_3 - \sqrt{(h_3 - h'_3)^2 + (2\Delta_2)^2}}{2} \tag{33}$$

$$\gamma = \frac{1}{2} \arcsin \frac{2\Delta_2}{\sqrt{(h_3 - h'_3)^2 + (2\Delta_2)^2}} \tag{34}$$

Next, a description is given regarding a case in which this device, with respect to the subject curved surface 1, is given a relative angular displacement $\xi$ around the main optical axis O.

Luminous spots $I_1''$, $I_2''$, $I_3''$, $I_4''$, $I_5''$, $I_6''$ are respectively projected onto the subject curved surface 1 by way of the projection optical systems 31, 32, 33, 34, 35, 36. Respective images $I_1^{*''}$, $I_2^{*''}$, $I_3^{*''}$, $I_4^{*''}$, $I_5^{*''}$, $I_6^{*''}$ of these luminous spots $I_1''$, $I_2''$, $I_3''$, $I_4''$, $I_5''$, $I_6''$ projected onto the subject curved surface 1 are respectively formed by the measuring optical system 40 on the light receiving surface 513 of the photoelectrical converter 50.

The photoelectrical converter 50 similarly outputs $\eta_x$, the projected distance on the image standard direction x of the interval of the image standard point O* and the images I*'', and $\eta_y$, the projected distance on the direction y at right angles to the image standard direction x on the light receiving surface 513. Namely, the distances $(\eta_{x1}'', \eta_{y1}'')$, $(\eta_{x2}'', \eta_{y2}'')$, $(\eta_{x3}'', \eta_{y3}'')$, $(\eta_{x4}'', \eta_{y4}'')$, $(\eta_{x5}'', \eta_{y5}'')$, $(\eta_{x6}'', \eta_{y6}'')$ are output which are projected in the x and y directions, and which respectively correspond to the images $I_1^{*''}, I_2^{*''}, I_3^{*''}, I_4^{*''}, I_5^{*''}, I_6^{*''}$.

A description is given below of the data processing in the calculating device 60 in this case. The calculating device 60 performs calculations to find the shape of the subject curved surface 1, based on each projected distance $h_1$ and $\Delta_1$ of the interval of the images $I_1^*$ and $I_2^*$, and on the projected distance $h_2$ in the x direction of the interval of the images $I_3^*$ and $I_4^*$, and on each projected distance $h_3$ and $\Delta_2$ of the interval of the images $I_5^*$ and $I_6^*$, and on each projected distance $h_1''$ and $\Delta_1''$ of the interval of the images $I_1^{*''}$ and $I_2^{*''}$, and on the projected distance $h_2''$ in the x direction of the interval of the images $I_3^{*''}$ and $I_4^{*''}$, and on the projected distance $h_3''$ in the x direction of the interval of the images $I_5^{*''}$ and $I_6^{*''}$.

Namely, the calculating device 60 respectively performs calculations to respectively find the two main meridian directions and the curvature in each meridian direction, for the regions of the subject curved surface 1 where the luminous spots $I_1$, $I_2$, $I_3$, $I_4$, and, $I_1''$, $I_2''$, $I_3''$, $_4''$ are respectively projected, based on $h_1$, $h_2$, $\Delta_1$, and, $h_1''$, $h_2''$, $\Delta_1''$. Moreover, the calculating device 60 performs calculations to find the relative angular displacement with respect to the subject curved surface 1, from the difference of the respective found directions for both of the two meridian directions of subject curved surface 1.

Furthermore, the calculating device 60 performs calculations to respectively find the two main meridian directions and the curvature in each meridian direction, for the regions of the subject curved surface 1 where the luminous spots $I_5$, $I_6$, $I_5''$, $I_6''$ are respectively projected, based on the relative angular displacement which has been found and on $h_3$, $\Delta_2$, and $h_3''$. A detailed description of these calculations is given below.

First, the above-mentioned $h_1''$, $h_2''$, $h_3''$, $\Delta_1''$, by way of the $(\eta_{x1}'', \eta_{y1}'')$, $(\eta_{x2}'', \eta_{y2}'')$, $(\eta_{x3}'', \eta_{y3}'')$, $(\eta_{x4}'', \eta_{y4}'')$, $(\eta_{x5}'', \eta_{y5}'')$, $(\eta_{x6}'', \eta_{y6}'')$ which are output from the photoelectrical converter 50, are written as:

$$h_1'' = \eta_{x1}'' + \eta_{x2}''$$

$$\Delta_1'' = \eta_{y1}'' + \eta_{y2}''$$

$$h_2'' = \eta_{x3}'' + \eta_{x4}''$$

$$h_3'' = \eta_{x5}'' + \eta_{x6}''$$

$$\Delta_2'' = \eta_{y5}'' + \eta_{y6}'' \tag{35}$$

When the relative angular displacement has been by an angle $\xi$ with respect to the subject curved surface 1, the projected distances $H_1''$, $H_2''$, $H_3''$ are respectively defined by way of $h_1''$, $h_2''$, $h_3''$:

$$H_1'' \equiv h_1''$$

$$H_2'' \equiv h_2''$$

$$H_3'' \equiv h_3'' \tag{36}$$

A case in which the direction of the main meridian $L_1$ forms an angle $\alpha$ with respect to the plane $\pi_1$ is similar to the discussion of the first timing above with respect to FIGS. 4–7. In this regard, the radii of curvature $r_1$, $r_2$ in the direction of the two main meridians $L_1$, $L_2$ of the region where the luminous spots $I_1$, $I_2$, $I_3$, $I_4$ of the subject curved surface 1 are projected, and the angle $\alpha$ which the main meridian $L_1$ makes with the plane $\pi_1$, are found by way of Equations (12), (13), (14).

Moreover, as the second timing, for the case in which the relative angular displacement has been made by an angle $\xi$ with respect to the subject curved surface 1, $h_1''$, $h_2''$, $\Delta_1''$ are represented by way of $H_1''$, $H_2''$, $\alpha_1''$:

$$h_1'' = H_2'' + (H_1'' - H_2'')\cos^2(\alpha'' + \xi) \tag{37}$$

$$h_2'' = H_2'' + (H_1'' - H_2'')\sin^2(\alpha'' + \xi) \tag{38}$$

$$\Delta_1'' = (H_1'' - H_2'')\sin(\alpha'' + \xi)\cos(\alpha'' + \xi) \tag{39}$$

From Equations (37), (38), (39), $H_1''$, $H_2''$, $\alpha''$ are represented by:

$$H''_1 = \frac{h''_1 + h''_2 + \sqrt{(h''_1 - h''_2)^2 + (2\Delta''_1)^2}}{2} \tag{40}$$

$$H''_2 = \frac{h''_1 + h''_2 - \sqrt{(h''_1 - h''_2)^2 + (2\Delta''_1)^2}}{2} \tag{41}$$

$$\alpha'' = \frac{1}{2} \arcsin \frac{2\Delta''_1}{|H''_1 - H''_2|} - \xi \tag{42}$$

From the image formation relationship in reflection, because $H_1''$ and $H_2''$ can be written:

$$H_1'' = 2\beta r_2 \sin\theta_1/2 \quad H_2'' = 2\beta r_1 \sin\theta_2/2 \tag{43}$$

the respective radii of curvature $r_1$, $r_2$ of the two meridian directions of the subject curved surface, and the angle $\alpha$ between the main meridian direction and the projection standard direction are given by the following:

$$r_1 = \frac{1}{2\beta\sin\frac{\theta_1}{2}} \frac{h''_1 + h''_2 + \sqrt{(h''_1 - h''_2)^2 + (2\Delta''_1)^2}}{2} \tag{44}$$

$$r_2 = \frac{1}{2\beta\sin\frac{\theta_2}{2}} \frac{h''_1 + h''_2 - \sqrt{(h''_1 - h''_2)^2 + (2\Delta''_1)^2}}{2} \quad (45)$$

$$\alpha'' = \frac{1}{2}\arcsin\frac{2\Delta''_1}{\sqrt{(h''_1 - h''_2)^2 + (2\Delta''_1)^2}} - \xi \quad (46)$$

The two main meridian directions $\Lambda_1$, $\Lambda_2$ of the region where the luminous spots $I_5$, $I_6$, $I_5''$, $I_6''$ of the subject curved surface 1 are projected as the main radii of curvature $\rho_1$, $\rho_2$ of the respective main meridian directions, and as an angle $\gamma$ which the main meridian direction $\Lambda_1$ forms within the plane $\pi_1$. Furthermore, $h_3$, $h_3''$, $\Delta_2$ are represented, by way of H, $H_3''$, $\gamma$, as follows:

$$h_3 = H_3'' + (H_3 - H_3'')\cos^2\gamma \quad (47)$$

$$h_3 = H_3'' - (H_3 - H_3'')\sin^2\gamma \quad (48)$$

$$\Delta_2 = (H_3 - H_3'')\sin\gamma\cos\gamma \quad (49)$$

and $H_3$, $H_3''$, $\gamma$ are found by way of Equations (47), (48), (49).

$$H_3 = \frac{h_3 + h''_3 + \sqrt{(h_3 - h''_3)^2 + (2\Delta_2)^2}}{2} \quad (50)$$

$$H''_3 = \frac{h_3 + h''_3 - \sqrt{(h_3 - h''_3)^2 + (2\Delta_2)^2}}{2} \quad (51)$$

$$\gamma = \frac{1}{2}\arcsin\frac{2\Delta_2}{|H_3 - H'_3|} \quad (52)$$

From the imaging relationship of reflection, because $$H_3 = 2\beta\rho_1\sin\phi/2 \quad (53)$$

$$H_3'' = 2\beta\rho_2\sin\phi/2$$

the following are found:

$$\rho_1 = \frac{1}{2\beta\sin\frac{\phi}{2}} \frac{h_3 + h''_3 + \sqrt{(h_3 - h''_3)^2 + (2\Delta_2)^2}}{2} \quad (54)$$

$$\rho_2 = \frac{1}{2\beta\sin\frac{\phi}{2}} \frac{h_3 + h''_3 - \sqrt{(h_3 - h''_3)^2 + (2\Delta''_2)^2}}{2} \quad (55)$$

$$\gamma = \frac{1}{2}\arcsin\frac{2\Delta''_2}{\sqrt{(h_3 - h''_3)^2 + (2\Delta''_2)^2}} \quad (56)$$

Below, as examples of an ophthalmologic device to which the present invention is a description is given of an example of a curvature measuring device which manually measures the shape of a cornea, by cojointly measuring curvature in the central portion and peripheral portion.

First Preferred Embodiment of the Present Invention

First, a description will be given of a first mode of embodiment of the present invention. This first preferred embodiment is applied to an ophthalmic instrument in order to measure curvature of a cornea as a subject curved surface 1.

Figure 9A:
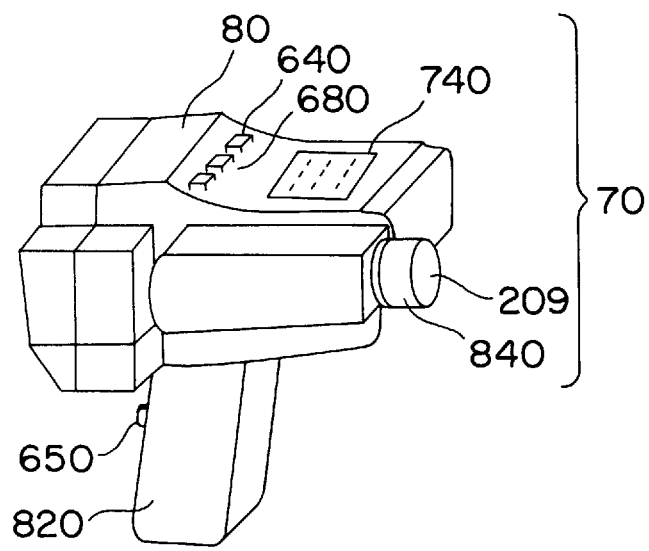
FIG. 9A is an elevated perspective view of an ophthalmologic curvature measuring device according to a preferred embodiment of the present invention.

First, an outline of the curvature measuring device in the present embodiment example is described with reference to FIG. 9A. FIG. 9A is an oblique drawing illustrating the external appearance of a curvature measuring device. In casing 80 of FIG. 10A, a grip 820 is disposed with its length direction along the vertical position when the curvature measuring device is to be maintained in a transverse position.

A measurement switch 650 is disposed in the grip 820 to receive instructions from an operator to commence measurement. Moreover, in the rear portion of casing 80, an eyepiece 840 is disposed for viewing through eyepiece lens 209 of the observation optical system 20. Moreover, a display device 70 is disposed in the curvature measuring device of the present embodiment example, to display guidance of the measurement, and moreover, in order to display the curvature of the measured cornea.

External display device 740 of the display device 70 is disposed in the top of casing 80. In the display device 70 of the present embodiment example, the external display device 740 is disposed in a portion seen from outside the casing 80, but is not so limited. For example, other than the above-mentioned external display device 740, a visual field display device 720 in the field of view displays the field of view of the observation optical device 20. In this case, by projecting on the focus plane 208 of the observation optical system 20 the image which is to be displayed while observing the cornea, measurement can be guided and measurement results can be confirmed.

Furthermore, in the curvature measuring device of the present embodiment example, a measurement range changeover switch 640 is disposed in order to select a central portion measurement mode for the measurement of the curvature of only the central portion of the cornea, or a peripheral measurement mode in order to measure conjointly the curvature of the central portion and the peripheral portion of the cornea.

Figure 9B:
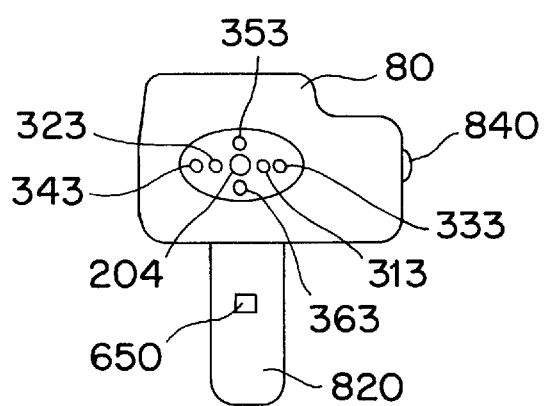
FIG. 9B is a side view of the ophthalmologic curvature measuring device illustrated in FIG. 9A.

A front view of the curvature measuring device of the present embodiment example is illustrated in FIG. 9B. In the front surface of this device, light beams from each of the projection optical systems 31, 32, 33, 34, 35, 36 illuminate the cornea. Moreover, apertures are provided to observe the light reflected by the cornea and to measure these images.

Figure 10A:
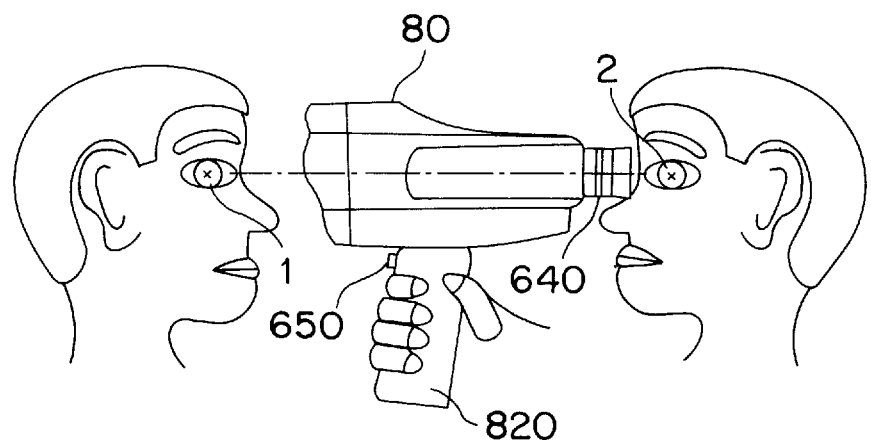
FIG. 10A is a side perspective view of a curvature measuring device in a vertical position according to a preferred embodiment of the present invention.
Figure 10B:
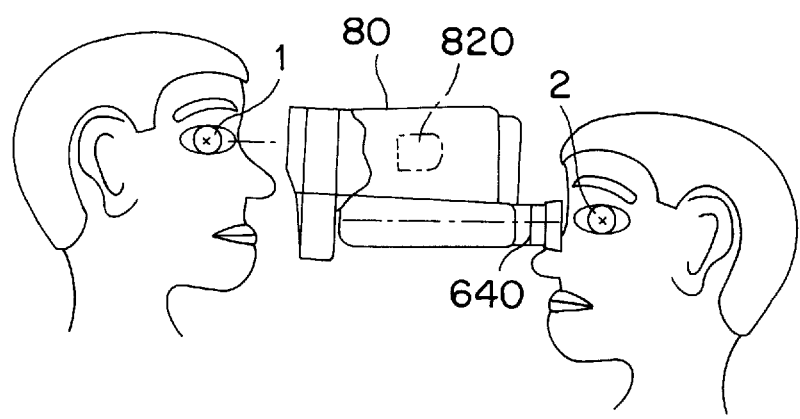
FIG. 10B is a side perspective view of a curvature measuring device in a horizontal position according to a preferred embodiment of the present invention.

FIGS. 10A and 10B are illustrative diagrams to show the state of cornea measurement in the present embodiment example. In FIG. 10A, the length direction of the grip 820 is kept perpendicular to the direction which joins both of the subject's eyes, showing the state in which a measurement is performed. Moreover, in FIG. 10B, the curvature measuring device is disposed with the length direction of the grip kept in a state along the direction joining both of the subject's eyes, showing the state in which measurement is performed.

With reference to the drawings, a description will be given of the visual field of the observation optical system through which the user looks, in the curvature measuring system of the present embodiment example.

Figure 11A:
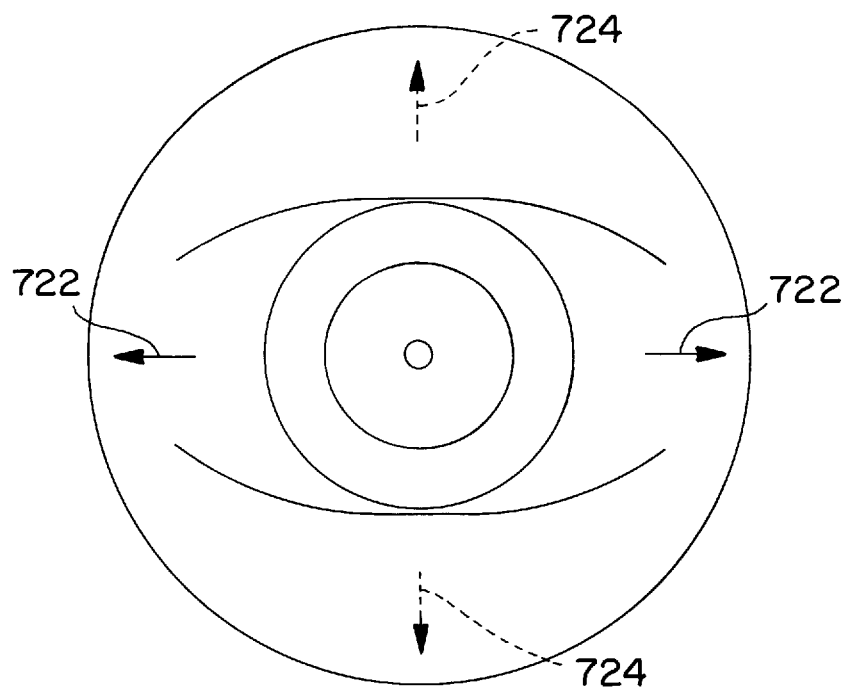
FIG. 11A is a schematic view of a visual field as observed through a curvature measuring device in a vertical position according to a preferred embodiment of the present invention.
Figure 11B:
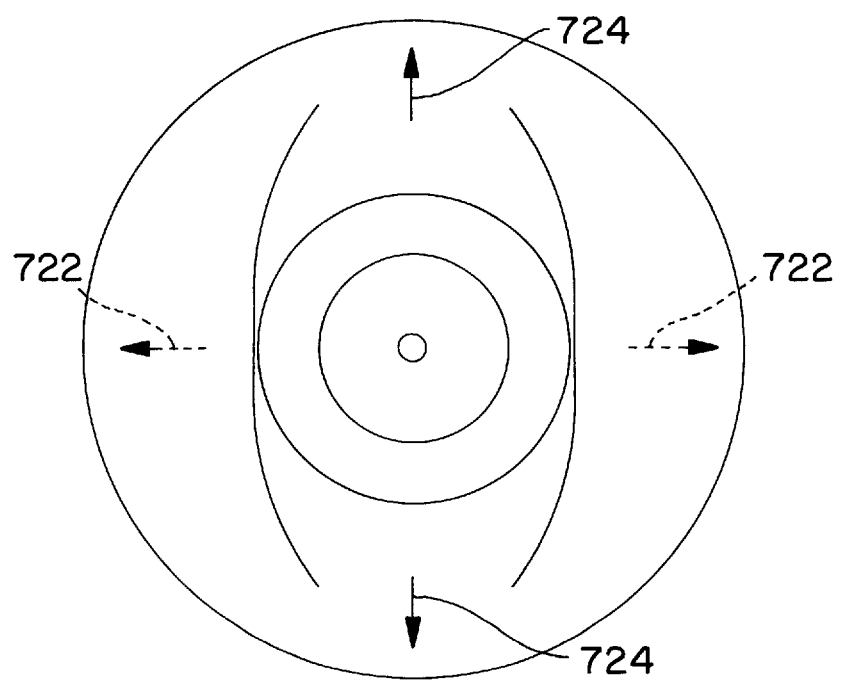
FIG. 11B is a schematic view of a visual field as observed through a curvature measuring device in a horizontal position according to a preferred embodiment of the present invention.

FIG. 11A is a visual field corresponding to the measurement state shown in FIG. 10A and FIG. 11B is a visual field corresponding to the measurement state shown in FIG. 10B. In the present embodiment example, a direction which is to coincide with the direction joining both of the subject's eyes, is denoted in the visual field by a pair of arrows 722. This is performed by making a display which emphasizes either of the pair of arrows 722. Specifically, for either of the pair of arrows which is along a direction which is to coincide with the direction joining both the subject's eyes, it can be emphasized by way of a difference of luminosity or a difference of hue. For simplicity, emphasis can be made by displaying with either of the arrow pairs displayed with high luminosity. Preferably, by performing a display which shows a position which is to correspond to main optical axis O, the center of the subject curved surface easily becomes kept in a state such that the main optical axis O passes through it.

In the curvature measuring device in the present embodiment example, in the visual field of the observation optical system 20, the direction along the plane $\pi_1$ is shown. Moreover, the image of the subject eye 1 is viewed via the objective lens 204 which is in common with the measuring optical system 40. The person performing the investigation, by looking at the image in the visual field of the observation optical system 20, can select the site of the subject eye 1 as the subject of the investigation.

The plane $\pi_1$, by being caused to be along the direction joining both eyes, becomes capable of projecting luminous spot(s) close to a site along one of the main meridian directions in the cornea. In the present embodiment example, the timing of measurements of a transverse position and a vertical position is instructed by way of a measurement switch 650 which has been disposed in the grip 820.

The present embodiment example can determine a relative angular displacement between the cornea and the curvature measuring device, based on the interval of the images of the luminous spots which have been projected onto the central portion of the cornea.

Figure 12:
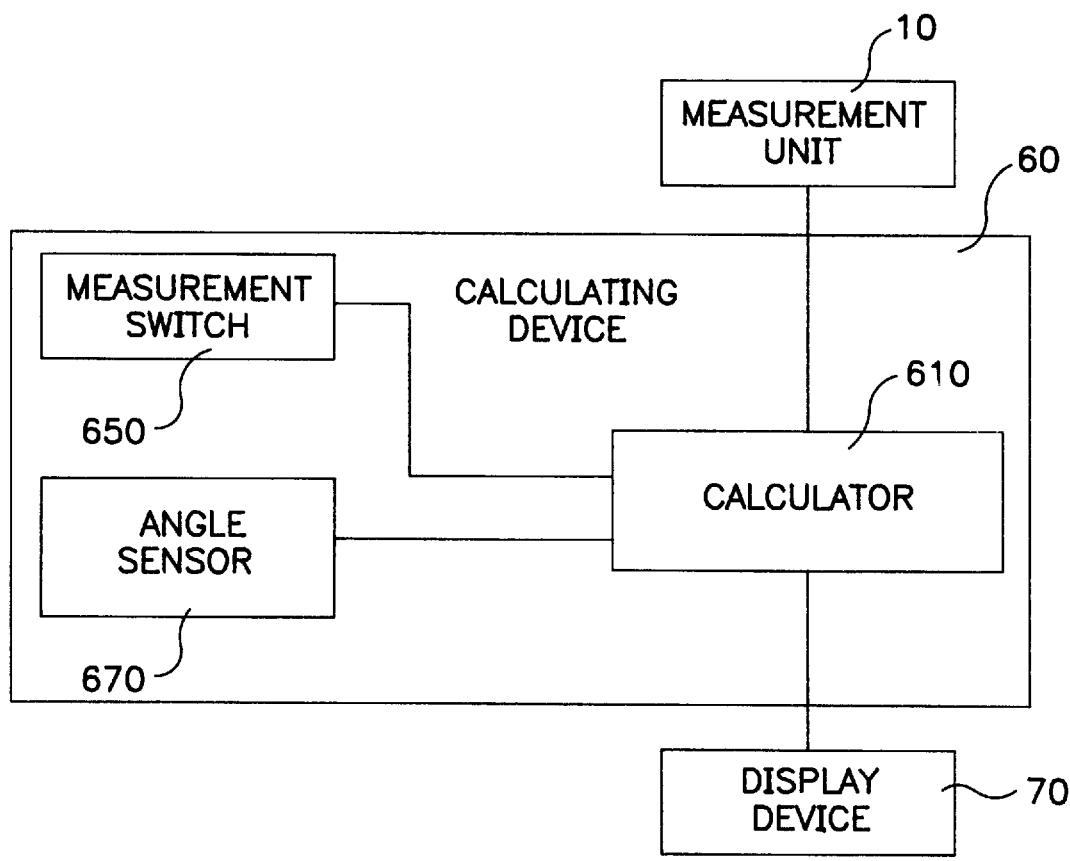
FIG. 12 is a block diagram of an ophthalmologic curvature measuring device according to a preferred embodiment of the present invention.
Figure 16:
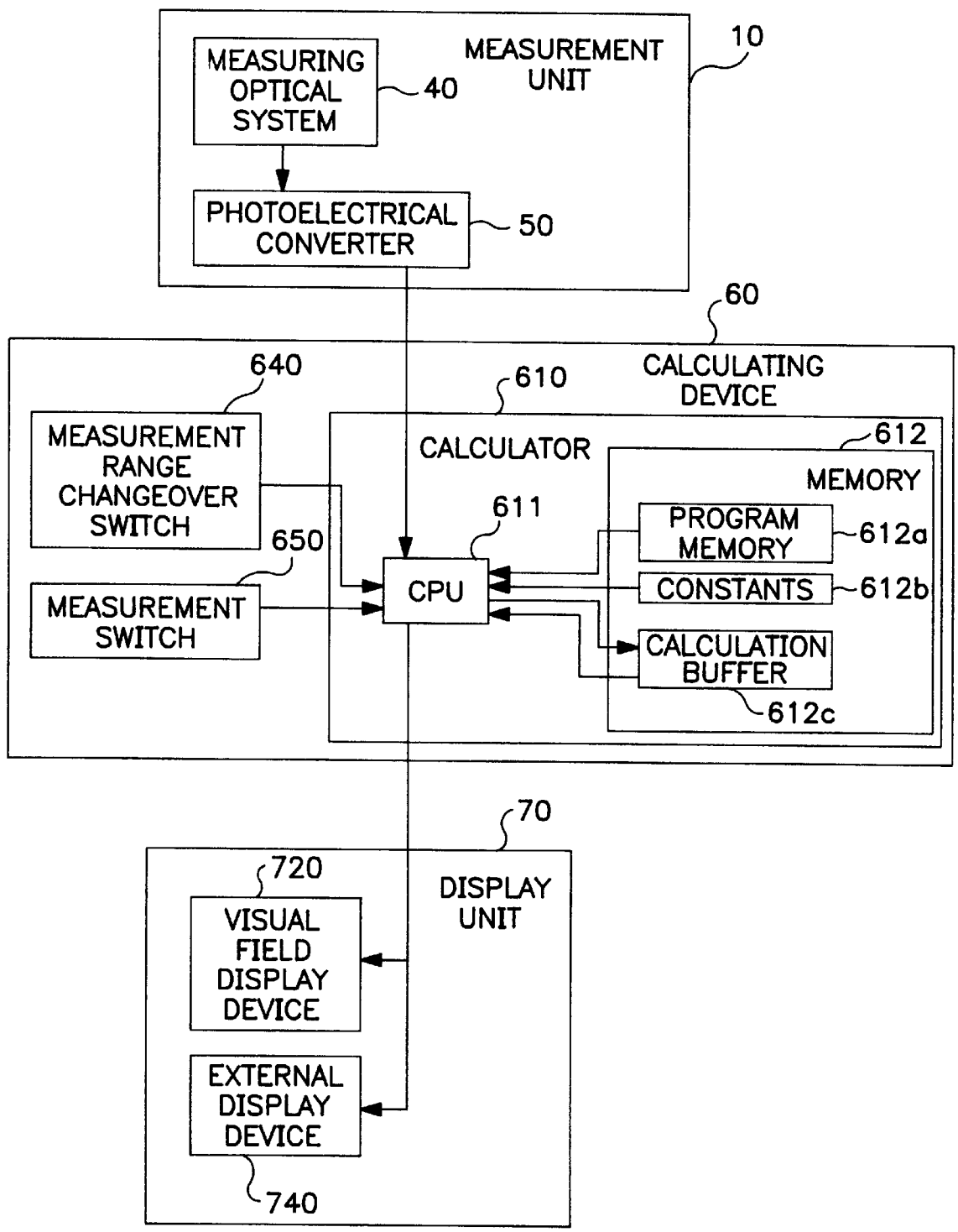
FIG. 16 is a block diagram of a measurement unit, a calculating device and a display device according to a first preferred embodiment of the present invention.
Figure 18:
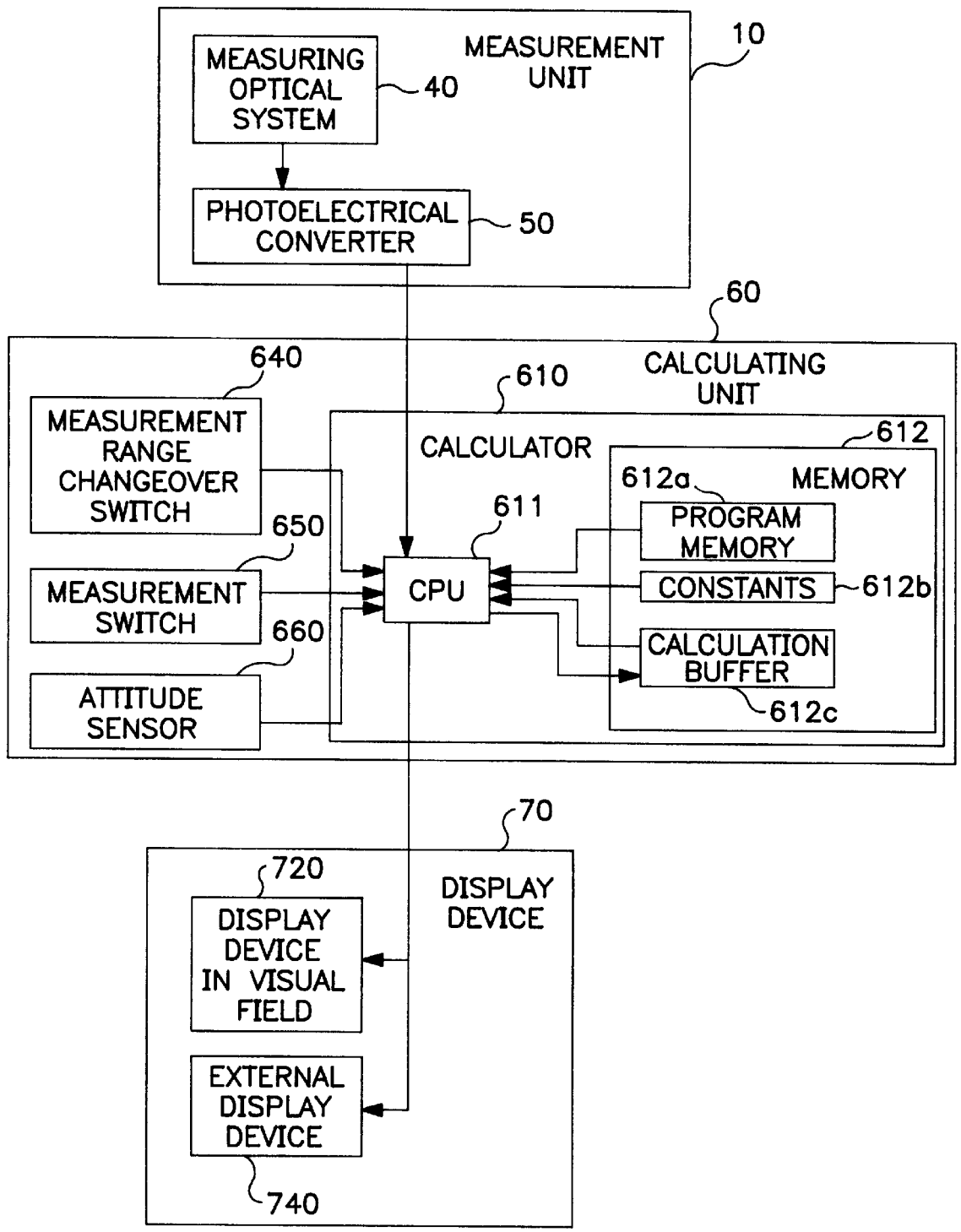
FIG. 18 is a block diagram of a measurement unit, a calculating device and a display device according to a second preferred embodiment of the present invention.

FIG. 12 relates to a summary of FIG. 16 and FIG. 18. A description will now be given of a curvature measuring device of the present embodiment example based on FIG. 16. The present curvature device is equipped with a measurement unit 10, a calculating device 60, and display device 70.

First, projecting luminous spots onto the cornea, in order to obtain data of this cornea image, data is sent from measurement unit 10 which includes the projection optical systems 31, 32, 33, 34, 35, 36, and the observation optical system 20, the measurement optical system 40, and the photoelectrical converter 50. The relationship between the positions of the optical images and the shape of the cornea is set forth above. Moreover, a calculating device 60 performs processing with respect to the intervals of the images which were measured by the measurement unit 10.

Calculator 610 is disposed in the calculating device 60 in order to perform calculation processes in the calculating device 60. A measurement switch 680 and a measurement range changeover switch 340 are disposed in order for the calculator 610 to receive instructions from the exterior. Moreover, in the calculator 610 are disposed a CPU 611 which performs processing and a memory 612. Memory 612 includes a program memory 612a in which the CPU 611 processing sequence is previously stored, and a constants memory 612b which contains previously stored constants, relationship tables and the like, which are read out when executing processing, and a calculation buffer 612 to temporarily store intermediate processed data in the course of execution of calculation processing.

The display device 70 displays the results of the calculations performed by the calculating device 60 and also displays instructions received externally. The display device 70 is equipped with external display device 740 in order to provide a display on the outside of the casing 80, and a visual field display device 720 in the visual field, in order to display in the visual field of the observation system 20.

Figure 13:
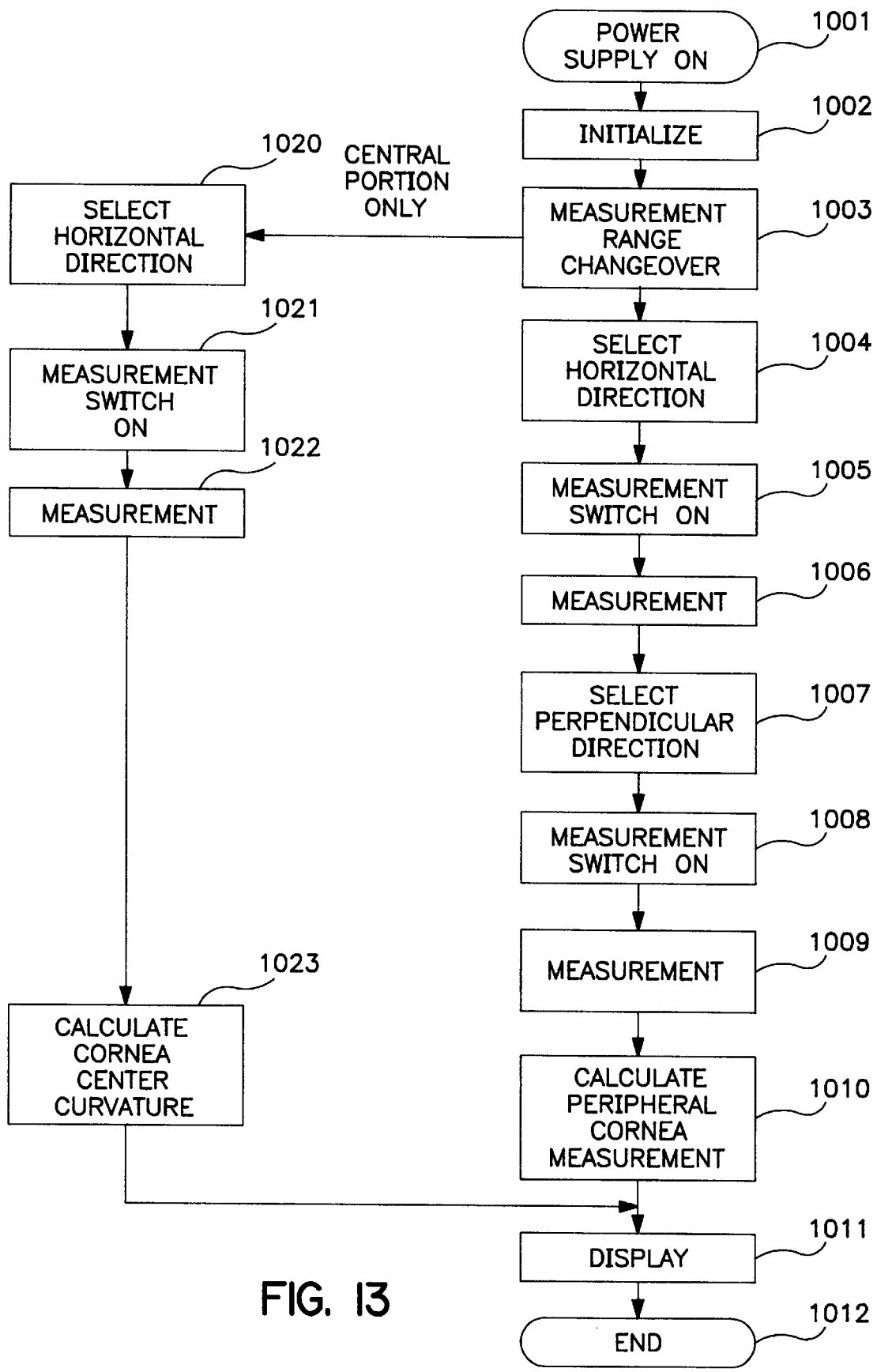
FIG. 13 is a flow diagram of measurement by an ophthalmologic curvature measuring device according to a preferred embodiment of the present invention.

FIG. 13 illustrates an operation sequence of the curvature measuring device in the present embodiment example, which an investigator is to perform. The curvature measurement state(s) of this curvature measuring device will be described with reference to FIG. 13.

First, the investigator introduces a power supply to the curvature measuring device (step 1001), and awaits initialization (step 1002). Next, he selects performing curvature measurement in only the central portion of the cornea, or conjointly in the central portion and in the peripheral portion (step 1003).

A description will first be given of the case of measuring the curvature in only the central portion of the cornea. With reference to the measured state making the plane $\pi_1$ horizontal in FIG. 1, in the display device in the visual field as in FIG. 11A, the arrow pair 722 is displayed with emphasis of the display (step 1020). The arrow pair 722 keeps the device in the transverse position by running in a direction joining both eyes.

Next, observing the image of the subject eye 1 formed by way of the observation optical system 20, the site for curvature measurement is selected. Causing the position which corresponds to the main optical axis O, which the visual field display device 720 shows in the visual field, to coincide with the center of the site to be measured of the subject eye 1, the measurement switch 650 is turned to the ON state (step 1021). Accompanying this, in step 1022, the reflected image(s) I in the cornea of the subject eye, which are the subject curved surface, are measured. Thereupon, based on the intervals of the abovementioned reflected images, the directions of the two main meridians, and, the radii of curvature in their directions, are calculated (step 1023) by way of the calculating device 60. The result of this calculation is displayed by display device 70 (step). In such a manner, the investigator can know the directions of the two main meridians of the subject eye 1, and the radii of curvature for these directions.

Next, in step 1004, the case is described in which performing curvature measurements in the center portion and in the peripheral portion of the cornea has been selected by way of the measurement range changeover switch 640.

In step 1005, such that the plane $\pi_1$ is taken as the horizontal direction, the curvature measuring device is maintained by display device 70. Namely, the arrow pair 722 in FIG. 11A are made to run along the direction joining both eyes thereby keeping the device in the transverse position.

By way of the observation optical system 20, selecting the measurement position of the subject curved surface 1, the images reflected in the subject curved surface 1 are measured (step 1006). Accompanying this, in step 1007, the curvature measuring device to be supported in the perpendicular direction is displayed. As shown in FIG. 11B, because the arrow pair 724 is given an emphasized display, the direction shown with regard to the arrow pair 724 maintains the device. The arrow pair 724 runs along the direction joining both eyes in the transverse position.

By switching the measurement switch ON (step 1008), the images reflected in the cornea are measured (step 1009). Accompanying this, in step 1006 and step 1009, based on the data of the images reflected in the measured cornea, in the calculating device 60, the two main meridian directions in the periphery of the cornea, and, the radii of curvature of the respective directions, are calculated (step 1010). These calculation results are displayed by the display unit in step 1011. In this manner, the investigator can know the two main meridian directions in the periphery of the cornea, and, the radii of curvature of the respective directions, in the periphery of the subject eye 1.

Figure 17:
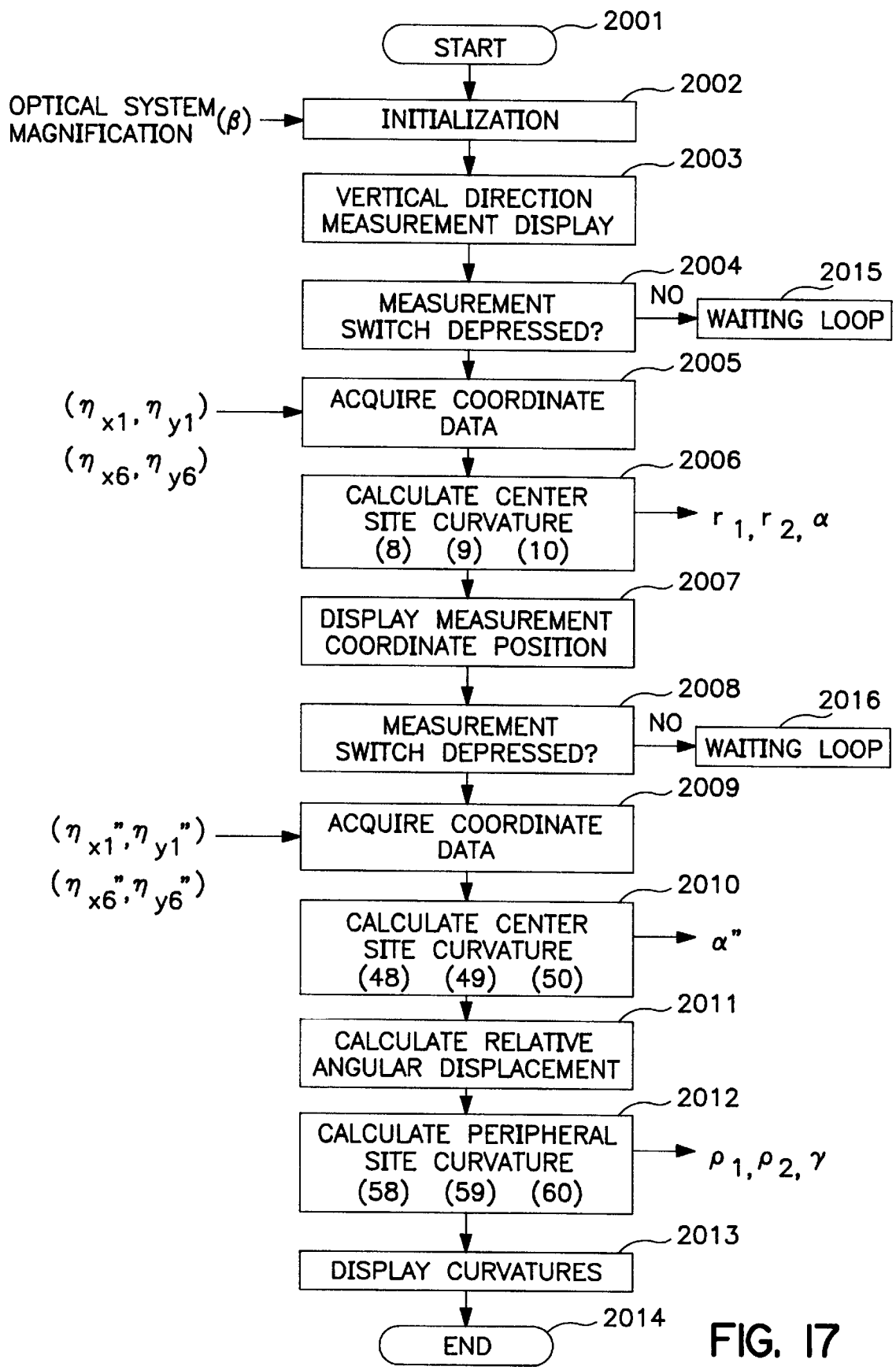
FIG. 17 is a flow diagram of curvature calculation according to a first preferred embodiment of the present invention.

A description centered on the calculation process which the calculating device 60 performs will next be given with reference to FIG. 17.

Processing is commenced in step 2001, and in the initialization in step 2002, the memory contents of the calculation buffer 612c are cleared, and the magnification β of the optical system, stored in the constants memory 612b, is read out. In step 2003, the arrow pair 722 is displayed by the visual field display device 720.

In step 2004, the process enters a waiting loop. The state of measurement switch 650 is monitored until measurement switch 650 is turned ON, thereby indicating instructions for measurement. When the measurement switch 650 is turned ON, the routine proceeds to the following step 2005.

In step 2005, the coordinates $(\eta_{x1}", \eta_{y1}")$, $(\eta_{x2}", \eta_{y2}")$, $(\eta_{x3}", \eta_{y3}")$, $(\eta_{x4}", \eta_{y4}")$, $(\eta_{x5}", \eta_{y5}")$, $(\eta_{x6}", \eta_{y6}")$ of the images $I_1^*, I_2^*, I_3^*, I_4^*, I_5^*, I_6^*$ formed by the measuring optical system 40 in the light receiving surface 513 shown in FIG. 14 are acquired from the photoelectrical converter 50. Next, in step 2006, the above coordinates are converted into data $h_1, h_2, h_3, \Delta_1, \Delta_2$ of intervals of images depending on Equation (1). Calculations are then performed according to Equations (12), (13) and (14) to find the first main meridian $L_1$ of the subject curved surface 1, and the angle $\alpha$ formed with the plane $\pi_1$. The first radius of curvature $r_1$ and the second radius of curvature $r_2$ are also found.

Next, in step 2007, the visual field display device 720 displays the arrow pair 724. In step 2008, operation of the system waits until the measurement switch 650 is depressed. When the measurement switch 650 is depressed, in step 2009, the coordinates $(\eta_{x1}', \eta_{y1}')$, $(\eta_{x2}', \eta_{y2}')$, $(\eta_{x3}', \eta_{y3}')$, $(\eta_{x4}', \eta_{y4}')$, $(\eta_{x5}', \eta_{y5}')$, $(\eta_{x6}', \eta_{y6}')$ of the images $I_1^{*\prime}, I_2^{*\prime}, I_3^{*\prime}, I_4^{*\prime}, I_5^{*\prime}, I_6^{*\prime}$ formed by the measurement optical system 40 are acquired from the measurement unit 10. In the next step 2010, depending on Equation (2), the above coordinates are converted to the data $h_1', h_2', h_3', \Delta_1', \Delta_2'$, i.e. intervals of images, depending on Equation (1). Calculations are then performed according to Equations (12), (13) and (14) to find the first main meridian $L_1$ of the subject curved surface 1 and the angle $\alpha'$ formed with the plane In step 2011, the relative angular displacement $\xi$ which occurred with respect to the subject curved surface 1 is found by way of the difference of the angle $\alpha$ which was found in step 2006, and the angle $\alpha'$ which was found in step 2010.

Then, in step 2012, based on the relative angular displacement $\xi$, $h_3$, $\Delta_2$, $H_3'$, according to Equations (54), (55) and (56), in the peripheral portion of the cornea, calculations are performed to find the angle $\gamma$ which the first main meridian of the subject curved surface forms with the plane $\pi_1$, and the radii of curvature $\rho_1$, $\rho_2$ in the two main meridian directions.

In step 2013, an instruction is given by the display device 70 to display $\gamma$, $\rho_1$, $\rho_2$ which were found as above-mentioned.

Moreover, here, the radius of curvature in the central portion, described for the case found in step 2006, but in step 2010, can be found according to Equations (44) and (45).

Second Preferred Embodiment of the Present Invention

Figure 19:
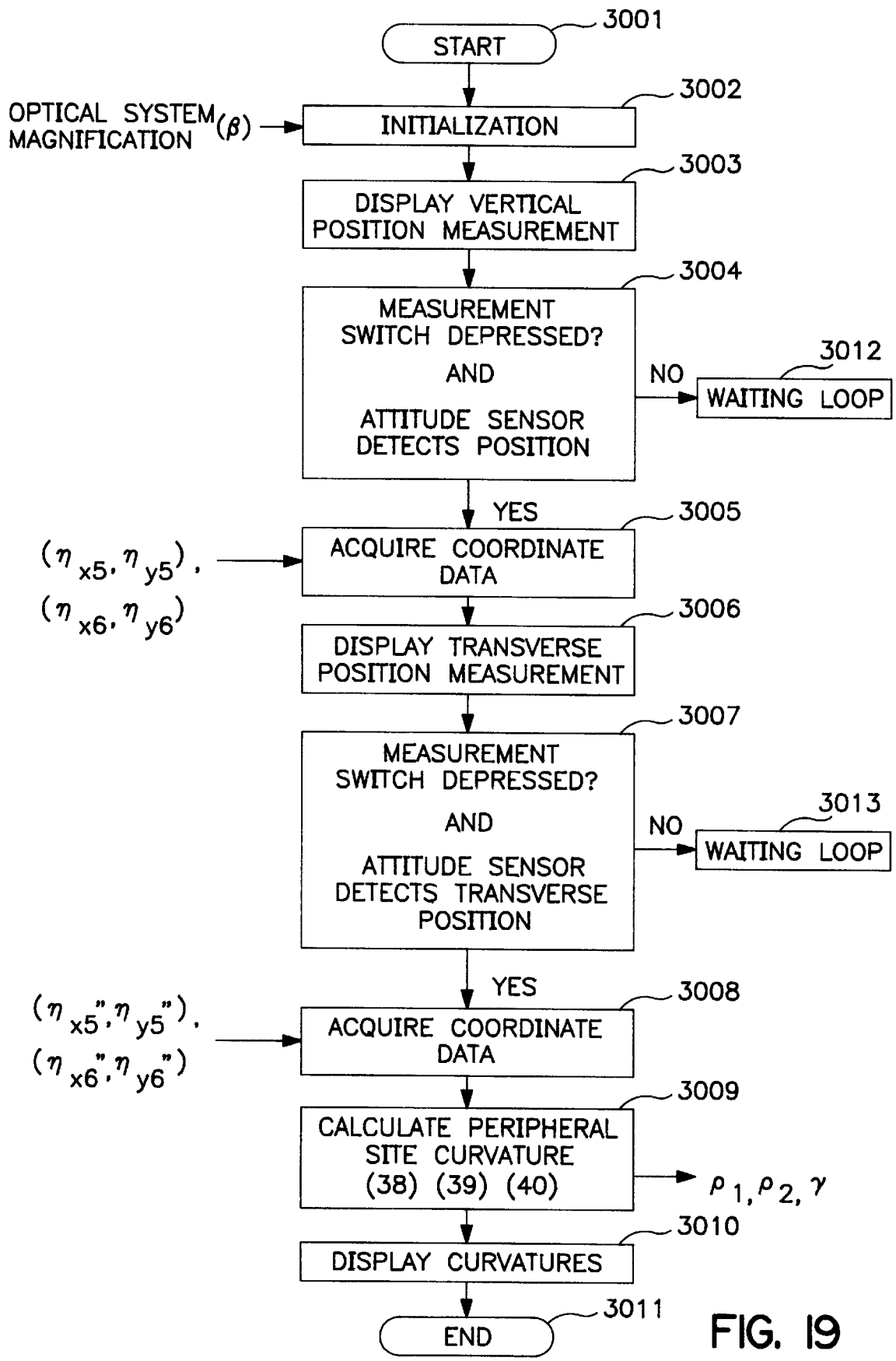
FIG. 19 is a flow diagram of curvature calculation according to a second preferred embodiment of the present invention.

A description will next be given of a second preferred embodiment of the present invention, with reference to FIGS. 18 and 19.

This embodiment example is a case of a curvature measuring device equipped with an attitude sensor 660 by way of gravity and the like, in order to detect the attitude with respect to the perpendicular axis of the curvature measuring device.

An outline of the measurements in this embodiment example will first be described.

The attitude sensor 660 at the point in time at which the attitude of the curvature measuring device reaches a predetermined state, outputs to the calculator 610 a signal to urge measurement. The calculator 610, due to this signal, specifies timing which acquires data of reflected images. The investigator, by way of the measurement switch 650, displays to cause agreement with a predetermined visual field in the observation optical system 20, a site as an investigation subject of the subject eye. Moreover, by way of the attitude sensor 660, an attitude in which the perpendicular axis becomes parallel to the plane $\pi_1$ (hereafter referred to as a "transverse position"), and an attitude in which the perpendicular axis is orthogonal to the plane $\pi_1$ (hereafter referred to as a "vertical position") are detected. Then, measurement switch 650 receives from the investigator an instruction urging measurement, and the attitude sensor 660 detects the attitude of the curvature measuring device to be the vertical position or the transverse position.

In the present embodiment example, the reflected image data is acquired exactly when the attitude of the curvature measuring device becomes the vertical position or the transverse position, by way of an operation of the measurement switch 650 receiving an instruction urging measurement, when the site which is to be the subject of measurement of the cornea is in the observation visual field.

Next, a description will be given of the sequence of processes centered on the calculating device 60 in the present embodiment example. With regard to the calculations to find the curvature of the central portion, because it is found similarly to the first embodiment example, a description of it is omitted.

First, when measurement is commenced in step 3001, the calculation buffer 612c is cleared in step 3002 and the magnification $\beta$ of the optical system is read in.

Next, in step 3003, an instruction is given to the display device 70 for emphasized display of the arrow pair 722 of the visual field display device 720 in the visual field, as shown in FIG. 11A.

After this, in step 3004, a waiting loop is entered for the state in which the measurement switch 650 and the attitude sensor simultaneously become ON. When the logical product of these outputs becomes ON, the routine proceeds to step 3005.

In step 3005, the coordinates $(\eta_{x5}, \eta_{y5})$, $(\eta_{x6}, \eta_{y6})$ on the light receiving surface 513 for the images $I_5, I_6$ are acquired. Next, in step 3006, for the display device 70, the arrow pair 724 of the visual field display device 720 in the visual field, as in FIG. 11B, is emphasized.

In step 3007, operation waits until the outputs from the measurement switch 650 and the attitude sensor 660 become ON. When the logical product becomes ON, in the next step 3008, the coordinates $(\eta_{x5}', \eta_{y5}')$, $(\eta_{x6}', \eta_{y6}')$ for the images $I_5', I_6'$ are acquired from the measurement unit 10.

After this, in step 3010, calculations are performed to find the angle $\gamma$ which the first main meridian makes with the plane $\pi_1$, and the first main radius of curvature $\rho_1$ and the second main radius of curvature $\rho_2$, according to Equations (32), (33) and (34), finding $h_3$, $h_3'$, $\Delta_2$ depending on Equation (2), from the coordinates $(\eta_{x5}, \eta_{y5})$, $(\eta_{x6}, \eta_{y6})$, $(\eta_{x5}', \eta_{y5}')$, $(\eta_{x6}', \eta_{y6}')$ of the images $I_5, I_6, I_5', I_6'$ acquired in steps 3005 and 3009.

In step 3011, the display device 70 is instructed to display the above-mentioned found results.

In this manner, data are displayed in the display device 70, including the meridian direction $\gamma$ of the first main meridian in the peripheral portion of the subject curved surface 1, and the two radii of curvature $\rho_1$, $\rho_2$ of the main meridian directions.

Third Preferred Embodiment of the Present Invention

Figure 20:
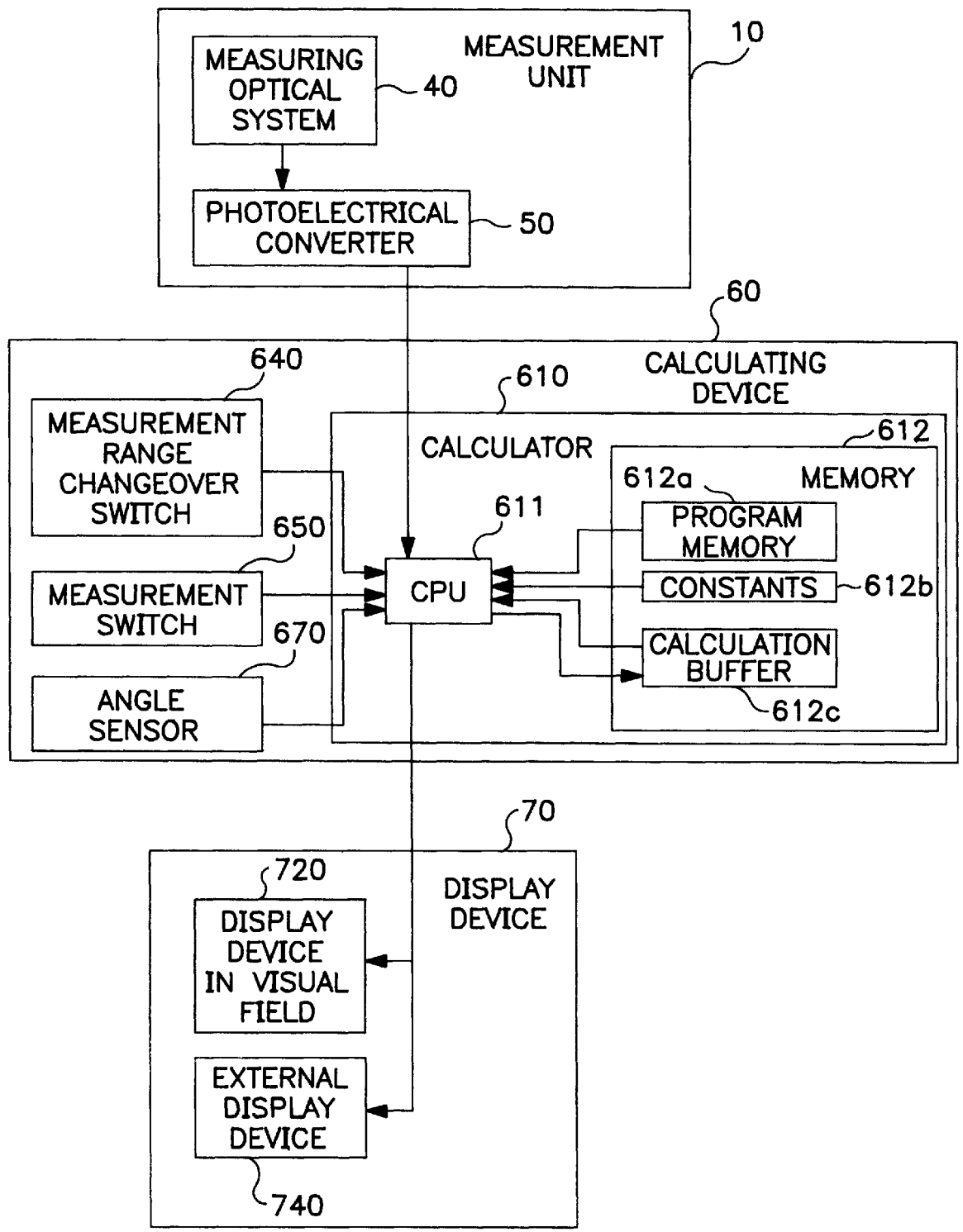
FIG. 20 is a block diagram of a measurement unit, a calculating device and a display device according to a third preferred embodiment of the present invention.

A description will next be given of a third preferred embodiment of the present invention, with reference to FIGS. 20 and 21. This preferred embodiment is similar to the first preferred embodiment in that a curvature measuring device is equipped with an angle sensor 670 to detect changes in attitude angle of the curvature measuring device.

The angle sensor 670 determines the angle of the curvature measuring device with respect to the perpendicular. The through which the curvature measuring device has changed in attitude is determined by measuring at the first timing and second timing. From a difference between these measured angles, the angle is determined. The angle found is then output to calculator 610.

An important difference of the third preferred embodiment from the second preferred embodiment is the attitude of the curvature measuring device. In the second preferred embodiment, when the transverse position or vertical position has been detected, measurement is performed. In contrast, in the present embodiment, measurements are performed at two optional timings and attitude changes are detected. Accordingly, in the present embodiment the state of the subject sometimes changes moment by moment and measurement timing is prioritized. Thus, in the case where a measurement has to be performed, the third preferred embodiment is particularly suitable.

Figure 21:
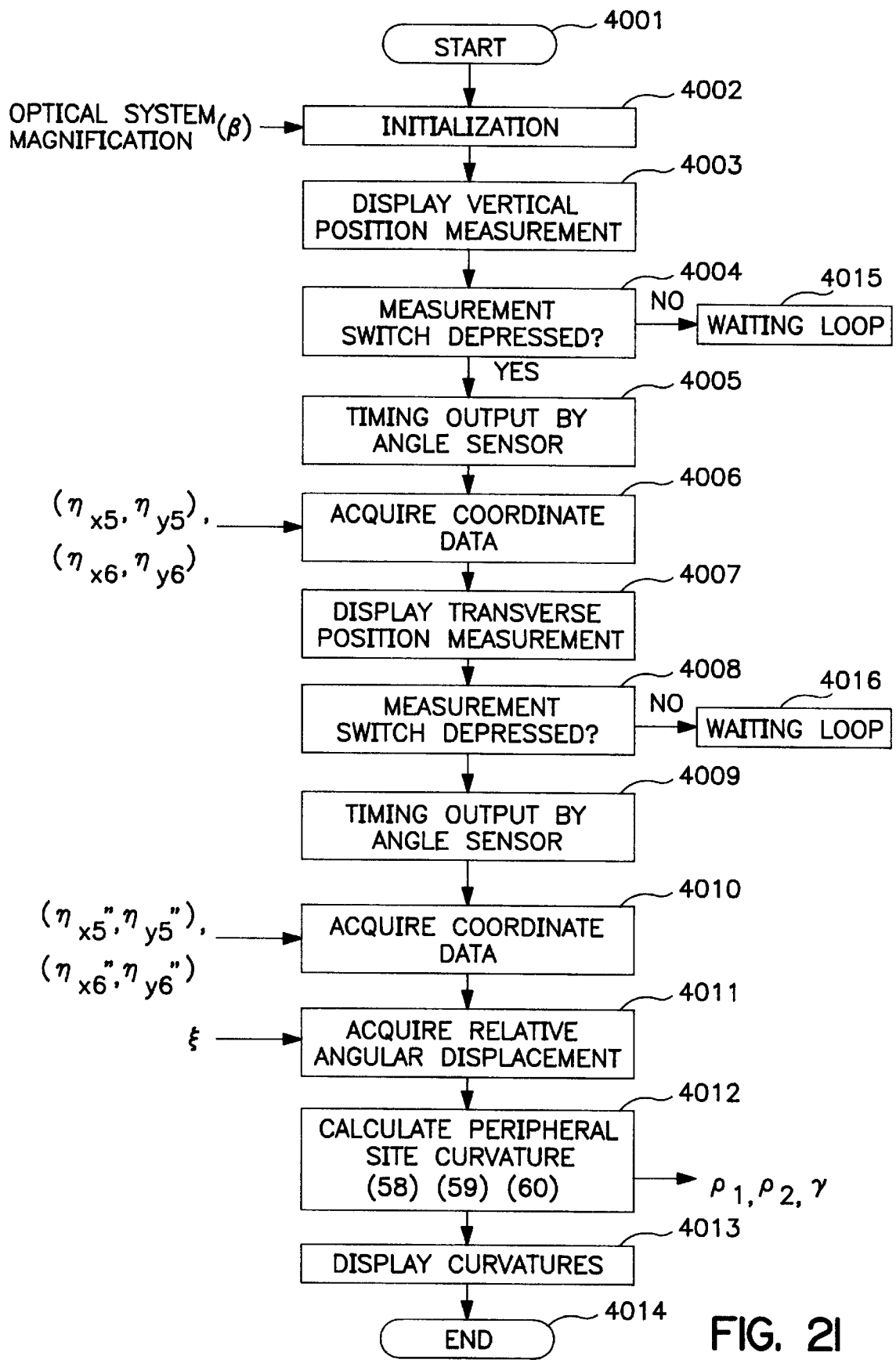
FIG. 21 is a flow diagram of a sequence of curvature calculation according to the third preferred embodiment of the present invention.

Next, with reference to FIG. 21, a description is given of a sequence of processes centered on calculating device 60. However, the calculations to determine curvature of the central portion are similar to the first embodiment and therefore a description is omitted.

First, when measurement is commenced in step 4001, the calculation buffer 612c is cleared in step 4002, moreover, the magnification $\beta$ of the optical system is read in. Next, in step 4003, an instruction is given to the display device 70 for emphasized display of the arrow pair 722 of the visual field display device 720 in the visual field, as shown in FIG. 11A. After this, in step 4004, a waiting loop is entered for the state in which the measurement switch 650 is turned ON. When the measurement switch 650 becomes ON, the routine proceeds to step 4005.

In step 4005, regarding the present attitude of the curvature measuring device, an instruction is output to the angle sensor 670, to measure the angle; in step 4006, the coordinates $(\eta_{x5},\eta_{y5})$, $(\eta_{x5},\eta_{y5})$ on the light receiving surface 513 for the images $I_5$, $I_6$ are acquired.

Next, in step 4007, for the display device 70, the arrow pair 724 of the visual field display device 720, is emphasized. In step 4008, output from the measurement switch 650 is monitored, awaiting the turning ON of measurement switch 650. When the output of the measurement switch 650 is turned ON, as step 4009, an instruction is output to the angle sensor to measure the angle, for the present attitude of the curvature measuring device.

In the next step 4010, the coordinates $(\eta_{x5}',\eta_{y5}')$, $(\eta_{x60}',\eta_{y6}')$ for the images $I_5'$, $I_6'$ are acquired from the measurement unit 10. Moreover, in step 4011, from the angle sensor 670, the angle $\xi$ is acquired, the attitude has changed between the measurement timings of step 4005 and step 4009.

After this, in step 4012, calculations are performed to find the angle $\gamma$ which the first main meridian makes with the plane $\pi_1$, and the first main radius of curvature $\rho_1$, and the second main radius of curvature $\rho_2$, according to Equations (54), (55) and (56), finding $h_3$, $h_3'$, $\Delta_2$ depending on Equation (2), from the coordinates $(\eta_{x5},\eta_{y5})$, $(\eta_{x6},\eta_{y6})$, $(\eta_{x5}',\eta_{y5}')$, $(\eta_{x6}',\eta_{y6}')$ of the images $I_5$, $I_6$, $I_5'$, $I_6'$ acquired in steps 4006 and 4010.

In step 4013, the display device 70 is instructed to display the above-mentioned found results. In this manner, data are displayed in the display device 70, including the meridian direction $\gamma$ of the first main meridian in the peripheral portion of the subject curved surface 1, and the two radii of curvature $\rho_1$, $\rho_2$ of the main meridian directions.

Although a few preferred embodiments of the present invention have been shown and described, it will be appreciated by those skilled in the art that changes may be made in these embodiments without departing from the principles and spirit of the invention, the scope of which is defined in the claims and their equivalents.

What is claimed is:

1. An ophthalmologic curvature measuring device to measure a curved surface, comprising:
   a first projection unit to project a first mark onto a first region of the curved surface;
   a second projection unit to project a pair of second marks onto a second region of the curved surface in the plane of the first mark and outside of the first region;
   an objective lens having an optical axis and transmitting a reflected image of the first mark and the second marks from the first and second regions of the curved surface;
   a measurement unit to receive the reflected image of the second marks from said objective lens, and to measure a first position of the second marks at a first timing and a second position of the second marks at a second timing different from the first timing;
   a displacement detecting unit to detect relative angular displacement of the measured first and second positions of the second marks about the optical axis of the objective lens; and
   a calculation unit to calculate curvature of the second region of the curved surface from the relative angular displacement detected by said displacement detecting unit.

2. The curvature measuring device according to claim 1, wherein
   the curved surface is the surface of a cornea,
   the first region is a corneal center portion of an eye to be measured, and
   the second region is a corneal peripheral portion of the eye to be measured.

3. The curvature measuring device according to claim 1, wherein
   the second projection unit includes first and second mark projection elements which respectively project a plurality of marks which constitute a pair, and
   the second mark projection element aligns a pair of eyes at a time of measurement along an assumed direction.

4. The curvature measuring device according to claim 1, further comprising:
   a position detecting unit to detect a position of the reflected image of the first mark based on values of the first and second timings,
   wherein the calculation unit calculates a diametral direction of the first region of the curved surface based upon a difference in respective diametral directions of the second marks which were found as the relative angular displacement of the measured positions of the first and second marks detected by said displacement detecting unit.

5. A curvature measuring device according to claim 1, wherein said displacement detecting unit detects an angular deviation exceeding a previously set range about an axis at right angles to the optical axis of the objective lens, and
said calculating unit determines that detection is impossible when the detected angular deviation exceeds the previously set range.

6. The curvature measuring device according to claim 5, wherein
the curved surface is the surface of a cornea,
the first region is a corneal center portion of an eye to be measured, and
the second region is a corneal peripheral portion of the eye to be measured.

7. The curvature measuring device according to claim 6, wherein the second projection unit includes first and second mark projection elements which respectively project a plurality of marks which constitute a pair, and the second mark projection element aligns a pair of eyes at a time of measurement along an assumed direction.

8. The curvature measuring device according to claim 1, wherein
the displacement detecting unit detects angular deviations from a perpendicular direction of curvature measuring from the respective first and second timing, and detects the relative angular displacement about the optical axis of the objective lens with respect to the curved surface from a difference of the respectively detected angular deviations.

9. The curvature measuring device according to claim 8, wherein
said displacement detecting unit detects an angular deviation exceeding a previously set range about an axis at right angles to the optical axis of the objective lens, and
said calculating unit determines that detection is impossible when the detected angular deviation exceeds the previously set range.

10. The curvature measuring device according to claim 8, wherein
said displacement detecting unit outputs signals measurement by said measurement unit when a direction joining the pair of second projected marks are parallel and at right angles to a perpendicular axis upon detection of relative angular displacement.

11. The curvature measuring device according to claim 1, further comprising:
an operating member to receive an operation indicating one of the first timing and second timing.

12. A curvature measurement method to measure curvature of a curved surface, comprising the steps of:
projecting a first light beam group onto a first region of a curved surface;
detecting reflected directions of the first light beam group from the curved surface;
determining a first shape index of the curved surface, including a principal meridian azimuth of two principal meridian directions of the curved surface, and curvature of the two principal meridian directions from the reflected directions of the first light beam group;
projecting a second group of light beams onto a second region of the curved surface outside the first region;
measuring a first reflected direction of the first light beam group and the second light beam group in the curved surface projected from a first azimuth about the principal axis of the curved surface;
measuring a second reflected direction of the first light beam group and the second light beam group in the surface projected from a second azimuth about the principal axis of the curved surface;
determining a second shape index of the curved surface from the first and second reflection directions of the first light beam group;
determining relative azimuth change about the principal axis of the curved surface from a difference of respective values of the two principal meridian directions;
converting standard directions of the measurements of the relative azimuth directions into first and second reflection directions of the second light beam group; and
determining curvature of the region of the curved surface from the first and second reflection directions.

13. The curvature measurement method according to claim 12, wherein
the first projected group of light beams include at least three light beams, and
the second light beam group includes at least two light beams projected onto the curved surface.

14. An ophthalmologic curvature measuring device to conjointly measure a central portion and a peripheral portion of a curved surface, comprising:
an observational optical system to observe a eye;
a first projection unit to project a pair of first marks onto the central portion of the curved surface;
a second projection unit to project a pair of second marks onto the peripheral portion of the curved surface in the plane of the first marks and outside of the first portion;
a third projection unit to project a pair of third marks onto the central portion of the curved surface in a plane perpendicular to the plane of the first marks;
a measurement unit to measure a first position of the first, second and third marks at a first timing and a second position of the first, second and third marks at a second timing;
a calculation unit to conjointly calculate curvature of the central portion and the peripheral portion of the curved surface from the measured first and second positions; and
an index display unit to selectively display an index of the first or second positions.

15. An ophthalmologic curvature measuring device to measure a curved surface, comprising:
a first projection unit to project a first mark onto a first region of the curved surface;
a second projection unit to project a pair of second marks onto a second region of the curved surface in the plane of the first mark and outside of the first region;
a measurement unit to measure a position of the first mark and to measure a position of the second marks at a first and second timing;
a displacement detecting unit to detect relative angular displacement of the measured position of the second marks at the first and second timing;
a position detecting unit to detect a position of the first mark based on the measured position measured by said measurement unit and the relative angular displacement detected by said displacement detecting unit; and
a calculation unit to calculate curvature of the second region of the curved surface from the relative angular displacement detected by said displacement detecting unit.

16. The curvature measuring device according to claim 15, wherein
the curved surface is the surface of a cornea,
the first region is a corneal center portion of an eye to be measured, and
the second region is a corneal peripheral portion of the eye to be measured.

17. The curvature measuring device according to claim 15, wherein
the second projection unit includes first and second mark projection elements which respectively project a plurality of marks which constitute a pair, and
the second mark projection element aligns a pair of eyes at a time of measurement along an assumed direction.

18. The curvature measuring device according to claim 15, wherein the calculation unit calculates a diametral direction of the first region of the curved surface based upon a difference of the respective diametral directions of the second marks which were found as the relative angular displacement detected by said displacement detecting unit.

19. The curvature measuring device according to claim 15, wherein
the displacement detecting unit detects angular deviations from a perpendicular direction of curvature measuring from the respective first and second timing, and detects the relative angular displacement about the optical axis of the objective lens with respect to the curved surface from a difference of the respectively detected angular deviations.

20. The curvature measuring device according to claim 15, wherein
said displacement detecting unit detects an angular deviation exceeding a previously set range about an axis at right angles to the optical axis of the objective lens, and said calculating unit determines that detection is impossible when the detected angular deviation exceeds the previously set range.

21. An ophthalmologic curvature measuring device to conjointly measure curvature of a central portion and a peripheral portion of a curved surface, comprising:
a first projection unit to project a first pair of marks onto the central portion of the curved surface;
a second projection unit to project a second pair of marks onto the peripheral portion of the curved surface in the plane of the first marks;
a third projection unit to project a third pair of marks onto the central portion of the curved surface;
a measurement unit to measure a first position of the first, second and third marks at a first timing and a second position of the first, second and third marks at a second timing; and
a calculation unit to calculate curvature of the peripheral portion of the curved surface from the measured positions of the first, second and third pair of marks taken at the first and second timing.

22. A device to conjointly measure curvature of a central portion and a peripheral portion of a cornea of an eye, comprising:
a first projection unit to project a first pair of marks onto the central portion of the cornea;
a second projection unit to project a second pair of marks onto the peripheral portion of the cornea;
a third projection unit to project a third pair of marks onto the central portion of the cornea;
a measurement unit to measure a first position of the first, second and third marks at a first timing and a second position of the first, second and third marks at a second timing; and
a calculation unit to calculate curvature of the central portion of the cornea and the peripheral portion of the cornea from the measured first, second and third marks at the first and second timing.

\* \* \* \* \*